(12) United States Patent
Haddad et al.

(10) Patent No.: US 12,083,345 B2
(45) Date of Patent: Sep. 10, 2024

(54) TIERED DETECTION OF TREATABLE EVENTS

(71) Applicant: Medtronic, Inc., Minneapolis, MN (US)

(72) Inventors: Tarek D. Haddad, Minneapolis, MN (US); Donald R. Musgrove, Minneapolis, MN (US); Andrew Radtke, Minneapolis, MN (US); Eric D. Corndorf, Minneapolis, MN (US); Paul J. DeGroot, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 266 days.

(21) Appl. No.: 17/383,170

(22) Filed: Jul. 22, 2021

(65) Prior Publication Data
US 2022/0023626 A1   Jan. 27, 2022

Related U.S. Application Data

(60) Provisional application No. 63/055,007, filed on Jul. 22, 2020.

(51) Int. Cl.
*A61N 1/365* (2006.01)
*A61N 1/362* (2006.01)
*A61N 1/372* (2006.01)

(52) U.S. Cl.
CPC .......... *A61N 1/365* (2013.01); *A61N 1/3621* (2013.01); *A61N 1/37223* (2013.01); *A61N 1/37235* (2013.01)

(58) Field of Classification Search
CPC .... A61N 1/3621; A61N 1/3622; A61N 1/365; A61N 1/37223; A61N 1/37235;
(Continued)

(56) References Cited

U.S. PATENT DOCUMENTS

| 4,458,691 A | 7/1984 | Netravali |
| 6,212,428 B1 | 4/2001 | Hsu et al. |

(Continued)

FOREIGN PATENT DOCUMENTS

| CN | 108030488 A | 5/2018 |
| EP | 1218060 B1 | 8/2004 |

(Continued)

OTHER PUBLICATIONS

International Preliminary Report on Patentability from International Application No. PCT/US2021/042807 dated Feb. 2, 2023, 8 pp.

(Continued)

*Primary Examiner* — Brian T Gedeon
(74) *Attorney, Agent, or Firm* — Shumaker & Sieffert, P.A.

(57) ABSTRACT

Techniques are disclosed for a multi-tier system for delivering therapy to a patient. In one example, a first device senses parametric data for a patient and determines, based on a first analysis of the parametric data, that the patient is experiencing a treatable event. In response, the first device establishes wireless communication with a second device and transmits the parametric data to the second device. The second device verifies, based on a second analysis of the parametric data, whether the patient is experiencing the treatable event. The second device selects, based on the second analysis of the parametric data, an instruction for responding to the treatable event and transmits the instruction for responding to the treatable event to the first device. In some examples, in response to receiving the instruction, the first device aborts delivery of therapy for the treatable event or proceeds with delivering therapy for the treatable event.

34 Claims, 6 Drawing Sheets

(58) Field of Classification Search
CPC ............ A61N 1/37258; A61N 1/39622; A61B 5/0031; A61B 5/333; A61B 5/361; A61B 5/363; A61B 5/686; A61B 5/7264
See application file for complete search history.

(56) References Cited

U.S. PATENT DOCUMENTS

| | | | |
|---|---|---|---|
| 6,308,094 | B1 | 10/2001 | Shusterman et al. |
| 6,594,523 | B1 | 7/2003 | Levine |
| 8,103,346 | B2 | 1/2012 | Mass et al. |
| 8,521,281 | B2 | 8/2013 | Patel et al. |
| 9,149,637 | B2 | 10/2015 | Warren et al. |
| 9,183,351 | B2 | 11/2015 | Shusterman |
| 9,585,590 | B2 | 3/2017 | McNair |
| 9,743,890 | B2 | 8/2017 | Lord et al. |
| 9,775,559 | B2 | 10/2017 | Zhang et al. |
| 10,463,269 | B2 | 11/2019 | Boleyn et al. |
| 10,888,282 | B2 | 1/2021 | Ong et al. |
| 2002/0016550 | A1 | 2/2002 | Sweeney et al. |
| 2002/0123768 | A1 | 9/2002 | Gilkerson et al. |
| 2006/0247709 | A1 | 11/2006 | Gottesman et al. |
| 2010/0179444 | A1 | 7/2010 | O'Brien et al. |
| 2010/0268103 | A1 | 10/2010 | McNamara et al. |
| 2010/0280841 | A1 | 11/2010 | Dong et al. |
| 2011/0270109 | A1 | 11/2011 | Zhang et al. |
| 2012/0004563 | A1 | 1/2012 | Kim et al. |
| 2012/0209126 | A1 | 8/2012 | Amos et al. |
| 2013/0274524 | A1 | 10/2013 | Dakka et al. |
| 2013/0274624 | A1 | 10/2013 | Mahanjan et al. |
| 2014/0142448 | A1 | 5/2014 | Bae et al. |
| 2014/0257063 | A1 | 9/2014 | Ong et al. |
| 2014/0378856 | A1 | 12/2014 | Koike et al. |
| 2015/0164349 | A1 | 6/2015 | Gopalakrishnan et al. |
| 2015/0265217 | A1 | 9/2015 | Penders et al. |
| 2016/0022164 | A1 | 1/2016 | Brockway et al. |
| 2016/0022166 | A1 | 1/2016 | Stadler |
| 2016/0135706 | A1 | 5/2016 | Sullivan et al. |
| 2016/0192853 | A1 | 7/2016 | Bardy et al. |
| 2016/0220137 | A1 | 8/2016 | Mahajan et al. |
| 2016/0232280 | A1 | 8/2016 | Apte et al. |
| 2017/0095673 | A1 | 4/2017 | Ludwig et al. |
| 2017/0105683 | A1 | 4/2017 | Xue |
| 2017/0156592 | A1 | 6/2017 | Fu |
| 2017/0196458 | A1 | 7/2017 | Ternes et al. |
| 2017/0290550 | A1 | 10/2017 | Perschbacher et al. |
| 2017/0347894 | A1 | 12/2017 | Bhushan et al. |
| 2017/0354365 | A1 | 12/2017 | Zhou |
| 2018/0008976 | A1 | 3/2018 | Okazaki |
| 2018/0089763 | A1 | 3/2018 | Okazaki |
| 2018/0146874 | A1 | 5/2018 | Walker et al. |
| 2018/0146929 | A1 | 5/2018 | Joo et al. |
| 2018/0233227 | A1 | 8/2018 | Galloway et al. |
| 2018/0279891 | A1 | 10/2018 | Miao et al. |
| 2018/0310892 | A1 | 11/2018 | Perschbacher et al. |
| 2019/0008461 | A1 | 1/2019 | Gupta et al. |
| 2019/0029552 | A1 | 1/2019 | Perschbacher et al. |
| 2019/0038148 | A1 | 2/2019 | Valys et al. |
| 2019/0038149 | A1 | 2/2019 | Gopalakrishnan et al. |
| 2019/0209022 | A1 | 7/2019 | Sobol et al. |
| 2019/0275335 | A1 | 9/2019 | Volpe et al. |
| 2019/0378620 | A1 | 12/2019 | Saren |
| 2020/0100693 | A1 | 4/2020 | Velo |
| 2020/0108260 | A1 | 4/2020 | Haddad et al. |
| 2020/0178825 | A1 | 6/2020 | Weijia et al. |
| 2020/0288997 | A1 | 9/2020 | Shute et al. |
| 2020/0352462 | A1 | 11/2020 | Pedalty et al. |
| 2020/0352466 | A1 | 11/2020 | Chakravarthy et al. |
| 2020/0352521 | A1 | 11/2020 | Chakravarthy et al. |
| 2020/0353271 | A1 | 11/2020 | Dani et al. |
| 2020/0357517 | A1 | 11/2020 | Haddad et al. |
| 2020/0357518 | A1 | 11/2020 | Musgrove et al. |
| 2020/0357519 | A1 | 11/2020 | Chakravarthy et al. |
| 2021/0137384 | A1 | 5/2021 | Robinson et al. |
| 2021/0204858 | A1 | 7/2021 | Attia et al. |
| 2021/0338134 | A1 | 11/2021 | Chakravarthy et al. |
| 2021/0338138 | A1 | 11/2021 | Pedalty et al. |
| 2021/0343416 | A1 | 11/2021 | Chakravarthy et al. |
| 2021/0345865 | A1 | 11/2021 | Spillinger et al. |
| 2023/0290512 | A1 | 9/2023 | Chakravarthy et al. |
| 2023/0320648 | A1 | 10/2023 | Chakravarthy et al. |
| 2023/0329624 | A1 | 10/2023 | Pedalty et al. |
| 2023/0330425 | A1 | 10/2023 | Haddad et al. |

FOREIGN PATENT DOCUMENTS

| | | | |
|---|---|---|---|
| EP | 2427105 | A1 | 3/2012 |
| JP | 2013524865 | A | 6/2013 |
| JP | 2012532633 | A | 7/2013 |
| JP | 2014100473 | A | 6/2014 |
| WO | 2010129447 | A1 | 11/2010 |
| WO | 2011008550 | A1 | 1/2011 |
| WO | 2013/160538 | A1 | 10/2013 |
| WO | 2017072250 | A1 | 5/2017 |
| WO | 2017091736 | A1 | 6/2017 |
| WO | 2018119316 | A1 | 6/2018 |
| WO | 2020049267 | A1 | 3/2020 |

OTHER PUBLICATIONS

"Visualize Features of a Convolutional Neural Network," MATLAB & Simulink, Mar. 15, 2018, 9 pp.
Classify ECG Signals Using Long Short-Term Memory Networks, MATLAB, retrieved from https://www.mathworks.com/help/signal/examples/classify-ecg-signals-using-long-short-term-memory-networks.html, Nov. 2, 2018, 19 pp.
Fawaz et al., "Deep learning for time series classification: a review," Irimas, Universite Haute Alsace, Dec. 7, 2018, 53 pp.
Kelwade et al., "Prediction of Cardiac Arrhythmia using Artificial Neural Network," International Journal of Computer Applications (0975-8887), vol. 115—No. 20, Apr. 2015, 6 pp.
Lau et al., "Connecting the Dots: From Big Data to Healthy Heart," HHS Public Access Author manuscript, Aug. 2, 2017, 5 pp.
Schwab et al., "Beat by Beat: Classifying Cardiac Arrhythmias with Recurrent Neural Networks," Mobile Health Systems Lab, Department of Health Sciences and Technology, Oct. 24, 2017, 4 pp.
U.S. Appl. No. 16/593,739, naming inventors: Haddad et al., filed Oct. 4, 2019.
"Visualize Features of a Convolutional Neural Network," MATLAB & Simulink, retrieved from https://www.mathworks.com/help/deeplearning/examples/visualize-features-of-a-convolutional-neural-network.html, Sep. 11, 2019, 7 pp.
Arrobo et al., "An Innovative Wireless Cardiac Rhythm Management (iCRM) System," Computer Science, 2014 Wireless Telecommunications Symposium, Jun. 2014, 5 pp.
International Search Report and Written Opinion of International Application No. PCT/US2021/042807, dated Oct. 29, 2021, 13 pp.
Sin et al., "Cardiac Arrhythmia Detection Using Deep Learning," Procedia Computer Science vol. 120, 2017 (Applicant points out, in accordance with MPEP 609.04(a), that the year of publication, 2017, is sufficiently earlier than the effective U.S. filing date, so that the particular month of publication is not in issue.) pp. 268-275.
Swerdlow et al., "Troubleshooting Implanted Cardioverter Defibrillator Sensing Problems I," Advances in Arrhythmia and Electrophysiology, vol. 7, No. 6, Dec. 2014, pp. 1237-1261.
Wartzek et al., "ECG on the Road: Robust and Unobtrusive Estimation of Heart Rate," IEEE Transactions on Biomedical Engineering, vol. 58, No. 11, Nov. 2011, pp. 3112-3120.
Chen et al., "Electrocardiogram Recognition Based on Variational AutoEncoder," Machine Learning and Biometrics, IntechOpen, Aug. 29, 2018, pp. 71-90.
Witten et al., "Data mining: Practical Machine Learning Tools and Techniques," Third Edition, Morgan Kaufmann, Feb. 3, 2011, 665 pp.
Andersen et al., "A Deep Learning Approach for Real-Time Detection of Atrial Fibrillation," Expert Systems with Applications, vol. 114, Aug. 14, 2018, pp. 465-473.
Anonymous, "Receiver Operating Characteristic—Wikipedia," Mar. 20, 2019, Retrieved from the Internet: URL: https://en.wikipedia.org/w/index.php?title=Receiver_operating_characteristic&oldis=888671034#History, 12 pp.

(56) References Cited

OTHER PUBLICATIONS

Habibzadeh et al., "On determining the most appropriate test cut-off value: the case of tests with continuous results," Biochemia Medica, Oct. 15, 2016, pp. 297-307.
Madani et al., "Fast and Accurate View Classification of Echocardiograms Using Deep Learning," Nature Partner Journals, vol. 1, No. 6, Mar. 21, 2018, 8 pp.
Schirrmeister et al., "Deep Learning with Convolutional Neural Networks for Brain Mapping and Decoding of Movement-Related Information from the Human EEG," Cornell University Library, Mar. 16, 2017, 58 pp.
U.S. Appl. No. 17/373,480, filed Jul. 2, 2021, by Chakravarthy et al.
U.S. Appl. No. 17/377,763, filed Jul. 16, 2021, by Chakravarthy et al.
U.S. Appl. No. 16/850,749, filed Apr. 16, 2020, by Pedalty et al.
U.S. Appl. No. 17/377,785, filed Jul. 16, 2020, by Pedalty et al.
Bresnick, "Machine Learning Algorithm Outperforms Cardiologists Reading EKGs", Health IT Analytics, Jul. 12, 2017, p. 5.
U.S. Appl. No. 18/479,228, filed Oct. 2, 2023, naming inventors Haddad et al.

TIERED DETECTION OF TREATABLE EVENTS

This application claims the benefit of U.S. Provisional Application No. 63/055,007, filed on Jul. 22, 2020, the entire content of which is incorporated herein by reference.

FIELD

This disclosure generally relates to medical devices and, more particularly, to detection of medical events by medical devices.

BACKGROUND

Medical devices may be external or implanted. Such medical devices may be used to detect medical events experienced by a patient, and in some cases deliver therapy to the patient to treat detected medical events. A diagnostic medical device may sense parametric patient data and periodically upload such data to, e.g., another medical device, a remote monitoring system, or a clinician or caregiver for review. Therapeutic medical devices may be used to treat various symptoms, diseases, or conditions, such as cardiac arrythmia, chronic pain, tremor, Parkinson's disease, epilepsy, urinary or fecal incontinence, sexual dysfunction, obesity, spasticity, gastroparesis, hypoglycemia or hyperglycemia, neurological or sleep disorders, etc. Therapeutic medical devices may deliver therapy in the form of electrical stimulation, mechanical stimulation, drug delivery, or other therapy delivery techniques.

SUMMARY

In general, the disclosure describes multi-tier techniques to identify a treatable event, such as a treatable arrhythmia in a patient. As described herein, a treatable event refers to an event for which therapy may be delivered to treat the treatable event. As examples, responsive to a medical device detecting a treatable event, the medical device may perform an action to treat the treatable event, such as deliver therapy to the patient or generating a notification to another medical device or a patient, clinician, or caregiver such that the other medical device or patient, clinician, or caregiver may provide therapy for the treatable event or a notification to the patient to, e.g., take medication.

In one example of the techniques of the disclosure, a first medical device (such as an IMD) senses parametric data for a patient. The IMD determines, based on the parametric data, that the patient is experiencing a treatable event. In response to detecting the treatable event, the IMD attempts to establish a wireless connection to a second medical device (e.g., an external device such as an external programmer or mobile device). If the IMD is unable to establish the wireless connection, the IMD may determine whether the IMD should attempt to treat the treatable event, such as by delivering therapy to the patient for the treatable event or issuing an alert or notification to another device or clinician that the treatable event has occurred.

If the IMD is able to establish the wireless connection, then IMD transmits at least a portion of the parametric data to the external device. The external device reviews the parametric data to confirm whether the patient is experiencing the treatable event. In some examples, the external device performs a more sophisticated analysis of the parametric data, analyzes a larger portion of the parametric data, or analyzes different aspects of the parametric data than the IMD so as to increase an accuracy in the determination of whether the patient is experiencing the treatable event. The external device selects an instruction for responding to the treatable event based on the second analysis and transmits the instruction to the IMD. For example, upon verifying that the patient is experiencing the treatable event, the external device instructs the IMD to proceed with delivery of therapy. In some examples, upon verifying that the patient is experiencing the treatable event, the external device instructs the IMD to generate a notification or alert indicative of the treatable event.

However, in response to determining that the patient is not experiencing the treatable event, the external device transmits, to the IMD, an instruction configured to cause the IMD to abort delivery of therapy to the patient. The IMD receives the instruction and aborts delivery of therapy to the patient, e.g., prior to delivery of therapy to the patient or during delivery of therapy to the patient. As another example, in response to determining that the patient is not experiencing the treatable event, the external device transmits, to the IMD, an instruction configured to cause the IMD to abort reporting of the treatable event. The IMD receives the instruction and does not generate a notification of the treatable event, e.g., prior to or during generation of the notification and/or transmission of the notification to a clinician or remote monitoring system.

In some examples, if the IMD is unable to establish the wireless connection, the IMD may analyze a relatively smaller amount of parametric data, and/or perform an analysis that requires a relatively shorter amount of time to complete. In this fashion, the IMD may classify an event as treatable or not treatable and rapidly determine whether to perform an action in response to the occurrence of the treatable event. However, if the IMD is able to establish the wireless connection, then the IMD may continue to sense parametric data and extend or continue performance of the first analysis while the external device performs the second analysis. For example, after establishing the wireless connection, the IMD may analyze a relatively larger amount of parametric data, and/or perform an analysis that requires a relatively longer amount of time to complete. This may allow the IMD to have higher specificity in classifying treatable events because more data is analyzed. Furthermore, the IMD may provide additional time to the external device such that the external device may have sufficient time to receive the parametric data, analyze the transmitted parametric data, verify the determination by the IMD to deliver therapy to the patient, and instruct the IMD whether to proceed with an action responsive to the occurrence of the treatable event.

Thus, the techniques disclosed herein may allow for enhanced patient care and increase the accuracy or specificity of treatable event detection in a patient. For example, the techniques disclosed herein enable the efficient use of sophisticated, but more computationally-intensive analysis of the parametric data so as to more accurately determine whether a treatable event has occurred in the patient, thereby increasing the likelihood that therapy delivered by the IMD is appropriate. Furthermore, by using an external device to perform computationally-intensive analysis of the parametric data, an IMD system as described herein may more accurately determine whether a treatable event has occurred in the patient without increasing the power consumption, size, or computational ability of the IMD.

In one example, this disclosure describes a method comprising: sensing, by a first device, parametric data for a patient; determining, by the first device and based on a first analysis of the parametric data, that the patient is experiencing a treatable event; in response to determining that the patient is experiencing the treatable event, determining, by the first device, whether a second device is available for wireless communication; in response to determining that the second device is available for wireless communication, transmitting, from the first device to the second device, at least a portion of the parametric data for a second analysis of the at least a portion of the parametric data by the second device; and receiving, by the first device and from the second device, an instruction for responding to the treatable event, the instruction selected based on the second analysis of the at least a portion of the parametric data by the second device.

In another example, this disclosure describes a first device comprising: sensing circuitry configured to sense parametric data for a patient; processing circuitry configured to: determine, based on a first analysis of the parametric data, that the patient is experiencing a treatable event; and in response to determining that the patient is experiencing the treatable event, determine whether a second device is available for wireless communication; and communication circuitry configured to: transmit, to the second device, at least a portion of the parametric data for a second analysis of the at least a portion of the parametric data by the second device in response to the determination that the second device is available for wireless communication; and receive, from the second device, an instruction for responding to the treatable event, the instruction selected based on the second analysis of the at least a portion of the parametric data by the second device.

In another example, this disclosure describes a method comprising: establishing, by a second device, wireless communication with a first device; receiving, by the second device and from the first device, parametric data for a patient; receiving, by the second device and from the first device, an indication that the first device has determined, based on a first analysis of the parametric data, that the patient is experiencing a treatable event; performing, by the second device, a second analysis of the parametric data to verify whether the patient is experiencing the treatable event; selecting, by the second device and based on the second analysis of the parametric data, an instruction for responding to the treatable event; and transmitting, by the second device and to the first device, the instruction for responding to the treatable event.

In another example, this disclosure describes a second device comprising: communication circuitry configured to: establish wireless communication with a first device; receive, from the first device, parametric data for a patient; and receive, from the first device, an indication that the first device has determined, based on a first analysis of the parametric data, that the patient is experiencing a treatable event; and processing circuitry configured to: perform a second analysis of the parametric data to verify whether the patient is experiencing the treatable event; and select, based on a second analysis of the parametric data, an instruction for responding to the treatable event, wherein the communication circuitry is further configured to transmit, to the first device, the instruction for responding to the treatable event.

In another example, this disclosure describes a system comprising: a first device configured to: sense parametric data for a patient; determine, based on a first analysis of the parametric data, that the patient is experiencing a treatable event; in response to determining that the patient is experiencing the treatable event, determine whether a second device is available for wireless communication; in response to determining that the second device is available for wireless communication, transmit, to the second device, at least a portion of the parametric data; and the second device configured to: receive the at least a portion of the parametric data; perform a second analysis of the at least a portion of the parametric data to verify whether the patient is experiencing the treatable event; and select, based on a second analysis of the parametric data, an instruction for responding to the treatable event; and transmit, to the first device, the instruction for responding to the treatable event, wherein the first device is further configured to: receive the instruction for responding to the treatable event.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Like reference characters refer to like elements throughout the figures and description.

DETAILED DESCRIPTION

Figure 1:
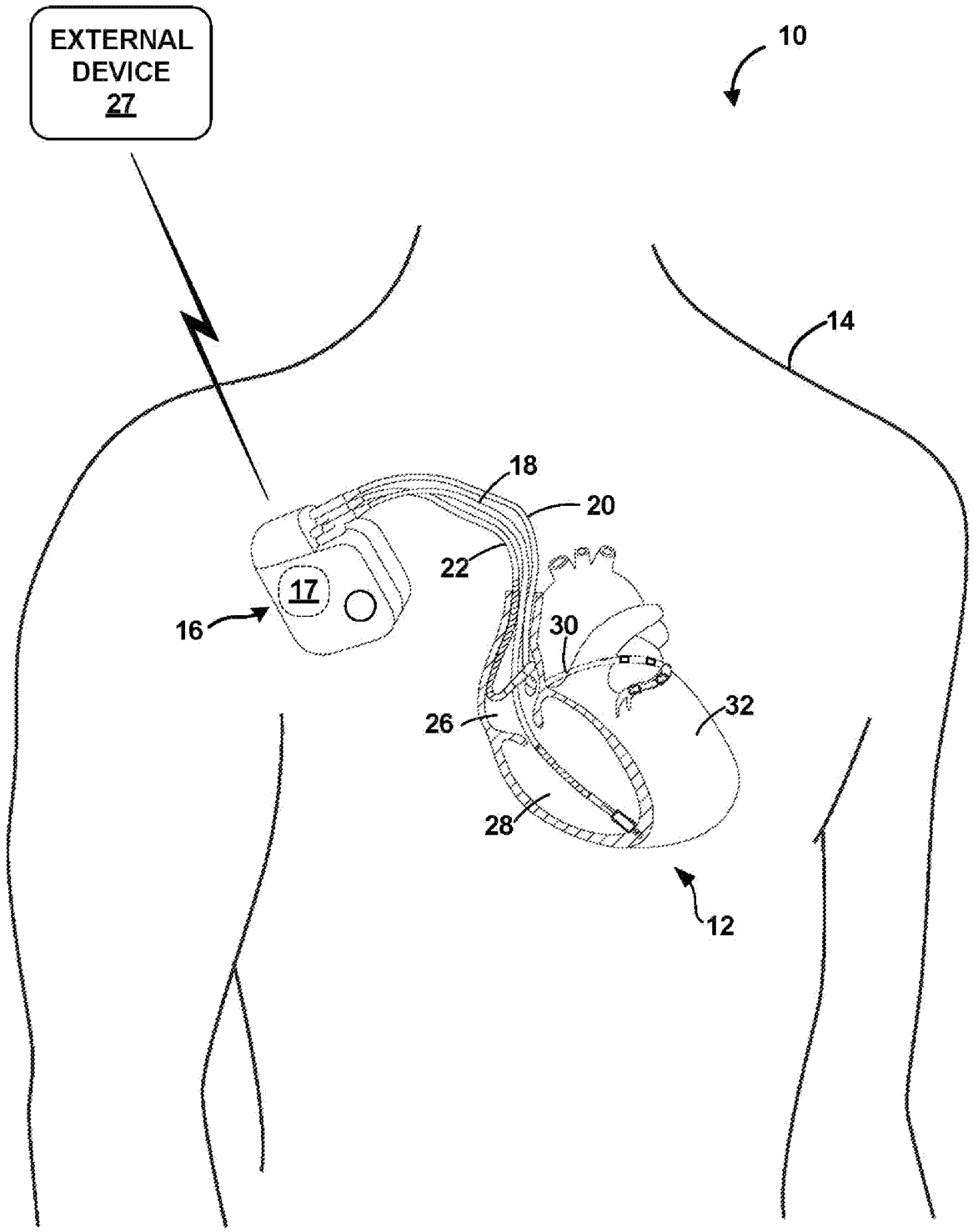
FIG. 1 is a block diagram illustrating an example system for detecting treatable events in accordance with the techniques of the disclosure.

Techniques are disclosed for a medical device system that provides improved specificity of detection of treatable events. In examples, where the medical device system is a therapy delivery system, the techniques set forth herein may enable such a medical device system to improve an evaluation of the appropriateness of delivery of therapy for such treatable events. In examples, where the medical device system is a diagnostics systems, the techniques set forth herein may enable such a medical device system to improve the accuracy of event detection and notification.

In some examples, the treatable events comprise cardiac arrhythmia events, including cardiac tachyarrhythmia such as ventricular tachyarrhythmia (VT) or ventricular fibrillation (VF), and an IMD is configured to treat such events by providing cardiac pacing therapy or defibrillation shock therapy or by generating a notification of the treatable event to inform another medical device, clinician, or the patient of the occurrence of the treatable event. Arrhythmia is a group of conditions in which a heartbeat of a heart of a patient is irregular. Arrhythmia may occur where the heartbeat is too slow (e.g., bradycardia) or too fast (e.g., tachycardia). Arrhythmia may take the form of, e.g., extra heartbeats, such as premature atrial contractions, premature ventricular contractions and premature junctional contractions, supraventricular tachycardias, ventricular arrhythmias and bradyarrhythmias; supraventricular tachycardias, such as atrial fibrillation, atrial flutter, or paroxysmal supraventricular tachycardia; or ventricular arrhythmias, such as ventricular fibrillation or ventricular tachycardia, or bradyarrhythmias.

If arrhythmia continues for more than a few seconds, it may result in cardiogenic shock and cessation of effective blood circulation. Consequently, sudden cardiac death (SCD) may result in a matter of minutes.

Most arrhythmias may be treated through the delivery of electrical stimulation. For example, a medical device may sense a treatable arrhythmia via one or more electrodes disposed on a lead and deliver electrical stimulation therapy, such as pacing pulses or an anti-tachycardia shock, via the one or more electrodes to treat the sensed arrhythmia. Such medical devices may be, e.g., a device external to the patient or an implantable medical device (IMD), such as an implantable cardioverter defibrillator (ICD) for the case of ventricular fibrillation. Electrodes coupled to the ICD may be placed within the heart, on the heart, or otherwise at locations that facilitate delivery of electrical therapy to the heart, such as intrathoracic locations outside of the heart, or subcutaneous, extrathoracic locations.

A medical device system as described herein includes a first device (e.g., an IMD) and a second device (e.g., an external device, such as an external programmer or a mobile device). The IMD senses parametric data for a patient. The IMD determines, based on the parametric data, that the patient is experiencing a treatable event. In response to detecting the treatable event, the IMD attempts to establish a wireless connection to the external device. If the IMD is unable to establish the wireless connection, the IMD may determine whether the IMD should take an action to respond to the treatable event, such as delivery of therapy for the treatable event, transmittal of a notification of the occurrence of the treatable event, etc.

If the IMD is able to establish the wireless connection, then IMD transmits at least a portion of the parametric data to the external device. The external device reviews the parametric data using an algorithm with high specificity to confirm whether the patient is experiencing the treatable event. In some examples, the external device performs a more sophisticated analysis of the parametric data, analyzes a larger portion of the parametric data, or analyzes different aspects of the parametric data than the IMD so as to increase an accuracy in the determination of whether the patient is experiencing the treatable event. For example, the external device may implement a machine learning system or other types of artificial intelligence. The external device selects an instruction for responding to the treatable event based on the second analysis and transmits the instruction to the IMD. For example, upon verifying that the patient is experiencing the treatable event, the external device instructs the IMD to proceed with responding to the treatable event, such as by delivering therapy to the patient. However, in response to determining that the patient is not experiencing the treatable event, the external device transmits, to the IMD, an instruction configured to cause the IMD to abort a response to the treatable event, such as by aborting delivery of therapy to the patient. The IMD receives the instruction and aborts delivery of therapy to the patient, e.g., prior to delivery of therapy to the patient or during delivery of therapy to the patient.

In some examples, the external device determines that the parametric data depicts a treatable event and so transmits an instruction to the IMD to proceed with responding to the treatable event, such as by delivering therapy for the treatable event. Alternatively, the external device may determine that the parametric data depicts a treatable event and take no action so as to allow the IMD to continue its procedures for responding to the treatable event, e.g., by delivering therapy for the treatable event. In some examples, the external device determines that the treatable event initially detected by the IMD is a false positive, and transmits an instruction causing the IMD to abort delivery of therapy. If the therapy has not occurred, the IMD terminates its therapy delivery procedures. In some examples, the external device determines that the parametric data does not depict a treatable event but too much time has passed such that the IMD has already taken an action, such as by delivering therapy. In this case, the external device may forgo instructing the IMD to abort therapy.

In some examples, if the IMD is unable to establish the wireless connection, the IMD may analyze a relatively smaller amount of parametric data, and/or perform an analysis that requires a relatively shorter amount of time to complete. In this fashion, the IMD may classify an event as treatable or not treatable and rapidly determine whether therapy should be delivered. As an example of the above, the treatable event may be a cardiac arrhythmia event. In this example, the IMD performs initial arrhythmia classification on sensed parametric data to identify a potential cardiac arrhythmia event. The initial arrhythmia classification may comprise, e.g., tachyarrhythmia classification using, e.g., 30 out of a previously sensed 40 heartbeats having an interval no greater than 320 milliseconds. If the IMD is unable to establish a wireless connection to the external device (e.g., such as where the external device is not within range of the IMD), the IMD may determine, based on the initial arrhythmia classification, to proceed with delivery of therapy.

In other examples, if the IMD is unable to establish the wireless connection, the IMD may continue analysis so as to analyze a relatively larger amount of parametric data so as to increase the accuracy of an initial classification of the treatable event. For example, the treatable event may be a cardiac arrhythmia event. In this example, the IMD performs initial arrhythmia classification on sensed parametric data to identify a potential cardiac arrhythmia event. The initial arrhythmia classification may comprise, e.g., tachyarrhythmia classification using, e.g., 30 out of a previously sensed 40 heartbeats having an interval no greater than 320 milliseconds. If the IMD is unable to establish a wireless connection to the external device (e.g., such as where the external device is not within range of the IMD), the IMD may continue to perform tachyarrhythmia classification using a longer determination time, e.g., 90 out of a previously sensed 120 heartbeats having an interval no greater than 320 milliseconds. In this example, if the additional analysis by the IMD verifies the initial classification, the IMD may proceed with delivery of therapy. However, if the additional analysis by the IMD does not verify the initial classification, the IMD may abort delivery of therapy. In this fashion, the IMD may offload additional analysis of the parametric data to the external device where possible, thereby decreasing the power usage by the IMD when the external device is within range to establish a wireless connection.

Additionally, if the IMD is able to establish the wireless connection, then the IMD may continue to sense parametric data and extend or continue performance of the first analysis while the external device performs the second analysis. For example, after establishing the wireless connection, the IMD may analyze a relatively larger amount of parametric data, and/or perform an analysis that requires a relatively longer amount of time to complete.

Continuing with the foregoing example of cardiac arrhythmia, upon establishing a wireless connection with the external device, the IMD continues to sense parametric data from the patient and extends performance of arrhythmia classification of the new parametric patient data while the external device performs the second analysis of the parametric data. For example, the IMD may continue to perform tachyarrhythmia classification using a longer determination time, e.g., 90 out of a previously sensed 120 heartbeats having an interval no greater than 320 milliseconds. By continuing the analysis of the parametric data while the external device performs the second analysis, the IMD may have higher specificity in classifying treatable events because more data is analyzed. Furthermore, the IMD may provide additional time to the external device such that the external device may have sufficient time to receive the parametric data, analyze the transmitted parametric data, verify the determination by the IMD to deliver therapy to the patient, and instruct the IMD whether to proceed with delivery of therapy.

In some examples, in response to determining that the continued analysis of the parametric data performed by the IMD indicates the treatable event, the IMD may proceed with delivery of therapy to the patient. In this fashion, the IMD may override the second analysis by the external device with the continued analysis by the IMD. This may be desirable where the second analysis performed by the external device is based on out-of-date parametric data, and where the continued analysis performed by the IMD is based on the most recent parametric data and is indicative of increasing severity of symptoms in the patient.

FIG. 1 is a block diagram illustrating an example system for detecting treatable events in accordance with the techniques of the disclosure. Medical device system 10 includes IMD 16 and external device 27. As illustrated by example system 10 in FIG. 1, IMD 16 may, in some examples, be an implantable cardiac pacemaker, implantable cardioverter/defibrillator (ICD), or pacemaker/cardioverter/defibrillator, for example. IMD 16 is connected to leads 18, 20 and 22. IMD 16 is communicatively coupled, e.g., capable of being selectively communicatively coupled, to external device 27. Although not illustrated in FIG. 1, external device 27 may be communicatively coupled to one or more computing devices over a communication network.

In patients with a high risk of ventricular fibrillation, the use of an ICD has been shown to be beneficial at preventing sudden cardiac death (SCD). Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes. An ICD is a battery powered electrical shock device. An ICD may include an electrical housing electrode (sometimes referred to as a can electrode), and is typically coupled to one or more other electrodes via electrical lead wires. Electrodes coupled to the ICD may be placed within the heart, on the heart, or otherwise at locations that facilitate delivery of electrical therapy to the heart, such as intrathoracic locations outside of the heart, or subcutaneous, extrathoracic locations.

If a tachyarrhythmia is sensed, the ICD may send a pulse via the electrodes to shock the heart and restore its normal rhythm. Some ICDs have been configured to attempt to terminate detected tachyarrhythmias by delivery of anti-tachycardia pacing (ATP) prior to delivery of a shock. Additionally, ICDs have been configured to deliver relatively high magnitude post-shock pacing after successful termination of a tachyarrhythmia with a shock, in order to support the heart as it recovers from the shock. Some ICDs also deliver bradycardia pacing, cardiac resynchronization therapy (CRT), or other forms of pacing.

Returning to FIG. 1, IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16. The therapy may be pacing, cardioversion and/or defibrillation pulses. IMD 16 may monitor EGM signals collected by electrodes on leads 18, 20 or 22, and based on the EGM signal, diagnose, and treat cardiac episodes, such as tachyarrhythmias.

In some examples, IMD 16 includes communication circuitry 17 including any suitable circuitry, firmware, software, or any combination thereof for communicating with another device, such as external device 27 of FIG. 1. For example, communication circuitry 17 may include one or more processors, memory, wireless radios, antennae, transmitters, receivers, modulation and demodulation circuitry, filters, amplifiers, or the like for radio frequency communication with other devices, such as external device 27. IMD 16 may use communication circuitry 17 to receive downlinked data from to control one or more operations of IMD 16 and/or send uplinked data to external device 27.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

While example system 10 of FIG. 1 depicts IMD 16, in other examples, the techniques of the disclosure may be applied to other types of medical devices that are not necessarily implantable. For example, a medical device in accordance with the techniques of the disclosure may include a wearable medical device or "smart" apparel worn by patient 14. For example, such a medical device may take the form of a wristwatch worn by patient 14, circuitry that is adhesively affixed to patient 14, or a wearable automated external defibrillator (WAED) In another example, a medical device as described herein may include an external medical device with implantable electrodes.

In some examples, external device 27 takes the form of an external programmer or mobile device, such as a mobile phone, a "smart" phone, a laptop, a tablet computer, a personal digital assistant (PDA), a wearable electronic device, a handheld computing device, computer workstation, server or other networked computing device, etc. In some examples, external device 27 is a CareLink™ monitor available from Medtronic, Inc. While depicted as a single device in the example of FIG. 1, in some examples, external device 27 comprises one or more computing devices that implement a remote monitoring or remote care system. A user, such as a physician, technician, surgeon, electrophysiologist, or other clinician, may interact with external device 27 to retrieve physiological or diagnostic information from IMD 16. A user, such as patient 14 or a clinician as described above, may also interact with external device 27 to program IMD 16, e.g., select or adjust values for operational parameters of IMD 16. External device 27 may include processing circuitry, a memory, a user interface, and communication circuitry capable of transmitting and receiving information to and from IMD 16.

IMD 16 and external device 27 may communicate via wireless communication using any techniques known in the art. Examples of communication techniques may include, for example, include radiofrequency (RF) telemetry, which may be an RF link established via an antenna according to Bluetooth® or Bluetooth® Low Energy (BLE)®, WiFi, or medical implant communication service (MICS), though other techniques are also contemplated. In some examples, external device 27 may include a programming head that may be placed proximate to the patient's body near the IMD 16 implant site in order to improve the quality or security of communication between IMD 16 and external device 27.

In accordance with the techniques of the disclosure, medical device system 10 implements a multi-tier system to determine whether to deliver therapy to patient 14. In one example, IMD 16 senses parametric data for patient 14. In some examples, IMD 16 senses cardiac electrogram data, such as an electrocardiogram (ECG), from patient 14. IMD 16 determines, based on the parametric data, that patient 14 is experiencing a treatable event and determines that IMD 16 should deliver therapy to patient 14. For example, IMD 16 determines that patient 14 is experiencing a cardiac arrhythmia event and determines that IMD 16 should deliver therapy, e.g., cardiac pacing or shock therapy. In response to detecting the treatable event, IMD 16 attempts to establish a wireless connection to external device 27. If IMB 16 is unable to establish the wireless connection to external device 27, IMD 16 proceeds to deliver therapy to patient 14.

If IMD 16 is able to establish the wireless connection to external device 27, then IMB 16 transmits at least a portion of the parametric data to external device 27. External device 27 reviews the parametric data to confirm whether patient 14 is experiencing the treatable event. In some examples, external device 27 analyzes a larger portion of the parametric data or different aspects of the parametric data than the IMD so as to increase an accuracy in the determination of whether the patient is experiencing the treatable event. The analysis performed by external device 27 may be more sophisticated or more computationally-intensive than IMD 16 and thereby provide greater specificity than the analysis by IMD 16. For example, IMD 16 may perform simple feature detection to identify the treatable event, whereas external device 27 may, e.g., analyze a larger portion of the parametric data than IMD 16 and/or apply a machine learning model to the parametric data. In some examples, external device 27 performs signal processing of the parametric data, such as a Fourier transform of multiple electrical signals to identify an indicative frequency shift or periodic pattern indicative of a treatable event. In some examples, external device 27 analyzes other types of information, such as electronic medical records (EMR) in conjunction with the patient parametric data (e.g. worsening heart failure or kidney failure recorded in a last doctor visit) or symptomatic information provided by a user, such as a clinician or patient, via a user interface.

External device 27 selects an instruction for responding to the treatable event based on the verification that the patient is experiencing the treatable event and transmits the instruction to IMD 16. For example, external device 27 confirms that the parametric data indicates patient 14 is experiencing the treatable event. In response to determining that the patient is experiencing the treatable event, external programmer 27 transmits an instruction to IMD 16 to proceed with delivery of therapy. However, in other examples, external device 27 determines that the parametric data does not indicate that patient 14 is experiencing the treatable event. In response to determining that patient 14 is not experiencing the treatable event, external programmer 27 transmits, to IMD 16, an instruction configured to cause IMD 16 to abort delivery of therapy to patient 14. IMD 16 receives the instruction from external programmer 27 and proceeds accordingly (e.g., by either delivering therapy for the treatable event or aborting delivery of therapy for the treatable event, as is the case). In examples where external programmer 27 instructs IMD 16 to abort therapy, IMD 16 may receive the instruction prior to delivery of therapy and aborts delivery of therapy to patient 14 without delivering therapy to patient 14. In other examples where external programmer 27 instructs IMD 16 to abort therapy, IMD 16 may receive the instruction during delivery of therapy and abort delivery of therapy to patient 14 during delivering therapy to patient 14. In still other examples, external device 27 determines that the parametric data does not indicate that patient 14 is experiencing the treatable event but IMD 16 is already delivering or has delivered therapy to patient 14, and so forgoes instructing IMD 16 to abort delivery of therapy. In this fashion, system 10 may act to increase an accuracy in the determination of whether patient 14 is experiencing the treatable event without increasing the computational complexity of IMD 16 and a commensurate increase in power consumption of IMD 16.

In the foregoing examples, system 10 is described as performing arrhythmia classification and determining whether patient 14 is experiencing a cardiac arrhythmia event. In such an example, cardiac arrhythmia events may be considered urgent events that require immediate delivery of therapy. For example, IMD 16 may determine that patient 14 is experiencing a cardiac arrhythmia event and request confirmation of the cardiac arrhythmia event from external device 27 within a short time period (e.g., seconds or minutes). In such an example, IMD 16 may elect to proceed with delivery of therapy if IMD 16 does not receive a response from external device 27 within a predetermined amount of time.

In other examples not specifically described herein, system 10 may perform detection and classification of other types of treatable events, both urgent and non-urgent. For example, for treatable events that are non-urgent, IMD 16 may request confirmation of a treatable event and wait until external device 27 confirms the presence of the treatable event prior to taking action. Such treatable events that are non-urgent may include, e.g., treatable events that are of insufficient magnitude to require intervention by IMD 16 (e.g., a minor, stable arrythmia that does not require delivery of an ATP shock or defibrillation shock) but may nevertheless warrant notification to a clinician to enable the clinician to adjust the therapy provided by IMD 16 (e.g., such as by adjusting one or more parameters defining cardiac pacing therapy) so as to provide more efficacious therapy to patient 14. For example, treatable events that are non-urgent may include a slow ventricular tachyarrhythmia that is hemodynamically stable, an instance of atrial fibrillation, worsening heart failure of the patient over time, or non-cardiac conditions, such as mild instances of hypoglycemia or hyperglycemia. For such non-urgent events, IMD 16 may wait minutes, hours, days, etc. so as to allow external device 27 to validate the determination of the non-urgent treatable event. The techniques of the disclosure allow IMD 16 to be tailored to use different criteria in determining whether to proceed with delivery of therapy upon detecting a treatable event or wait until IMD 16 receives confirmation of the treatable event from external device 27 according to various "decide and act" or "wait and see" methodologies.

In the example of FIG. 1, IMD 16 is described as a therapy delivery device. However, in other examples, IMD 16 may be a diagnostic device, such as a device that senses parametric patient data and uploads such data to a remote monitoring center for analysis or review by a clinician. In such an example, in response to detecting a treatable event, IMD 16 attempts to establish a wireless connection to external device 27. If IMD 16 is unable to establish the wireless connection to external device 27, IMD 16 proceeds to generate a notification of the occurrence of the treatable event. If IMD 16 is able to establish the wireless connection to external device 27, then IMD 16 transmits at least a portion of the parametric data to external device 27. External device 27 reviews the parametric data to confirm whether patient 14 is experiencing the treatable event. If external device 27 confirms that the parametric data indicates patient 14 is experiencing the treatable event, external programmer 27 transmits an instruction to IMD 16 to proceed with generation of the notification of the occurrence of the treatable event. In some examples, external programmer 27 may itself generate and transmit a notification of the occurrence of the treatable event, e.g., to a patient, clinician, caregiver, or remote monitoring system. However, if external device 27 determines that the parametric data does not indicate that patient 14 is experiencing the treatable event, external programmer 27 transmits, to IMD 16, an instruction configured to cause IMD 16 to abort generation of the notification of the occurrence of the treatable event. A clinician or another device may use the notification of the occurrence of the treatable event as a basis to initiate delivery of therapy to patient 14. In this fashion, system 10 may act to increase an accuracy in the detection of treatable events as well as the generation of notifications of such treatable events.

Medical device system 10 is described as including IMD 16 and external device 27. However, the techniques of the disclosure may be used with various other types and combinations of devices other than IMD 16 and external device 27. For example, medical device system 10 may implement the techniques of the disclosure with a first device and a second device, each of which may be, for example, any combination of implantable or external devices, such as a mobile phone, a "smart" phone, a laptop, a tablet computer, a personal digital assistant (PDA), a wearable electronic device, a handheld computing device, computer workstation, an external programmer, external therapy or monitoring device, or an IMD.

Thus, the techniques disclosed herein may allow for enhanced patient care and increase the accuracy or specificity of treatable event detection in a patient. For example, the techniques disclosed herein enable the efficient use of sophisticated, but more computationally-intensive analysis of the parametric data so as to more accurately determine whether a treatable event has occurred in the patient, thereby increasing the likelihood that therapy delivered by the IMD is appropriate. Furthermore, by using an external device to perform computationally-intensive analysis of the parametric data, an IMD system as described herein may more accurately determine whether a treatable event has occurred in the patient without increasing the power consumption, size, or computational ability of the IMD and enabling the IMD to take advantage of the increased computational ability of the external device.

Figure 2:
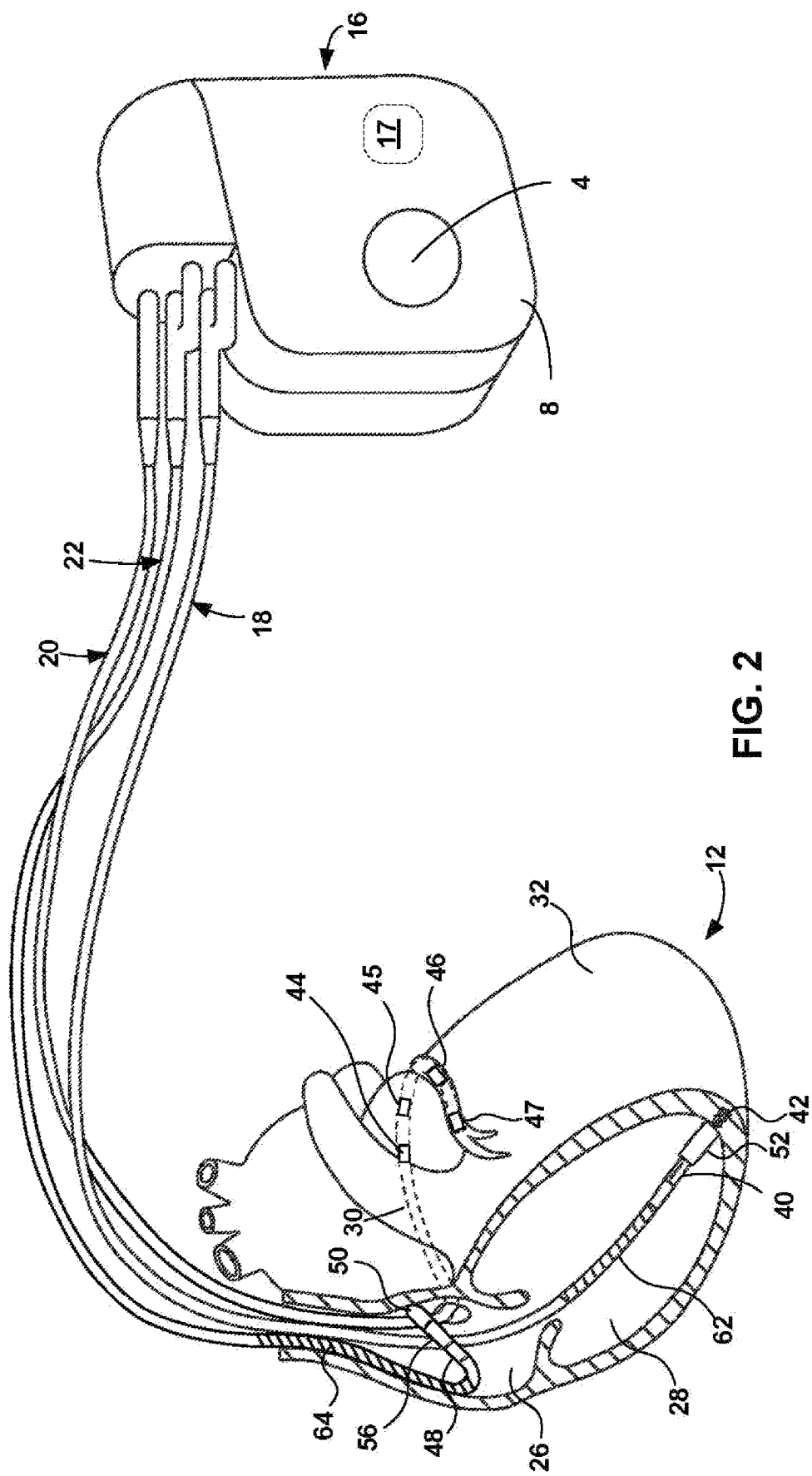
FIG. 2 is a conceptual diagram illustrating the IMD and leads of the system of FIG. 1 in greater detail.

FIG. 2 is a conceptual diagram illustrating IMD 16 and leads 18, 20, 22 of system 10 of FIG. 1 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 comprises segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40 and 44-48 take the form of ring electrodes, and electrodes 42 and 50 may take the form of extendable helix tip electrodes mounted retractably within insulative electrode heads 52 and 56, respectively. In some examples, each of electrodes 40, 42, 44-48, and 50 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

Housing 8 encloses signal generation circuitry that generates therapeutic signals, such as cardiac pacing, cardioversion, and defibrillation pulses, as well as sensing circuitry for sensing electrical signals attendant to the depolarization and repolarization of heart 12. Housing 8 may also enclose a memory for storing the sensed electrical signals. Housing 8 may also enclose a communication circuitry 17 for communication between IMD 16 and external device 27.

IMD 16 senses electrical signals attendant to the depolarization and repolarization of heart 12 via electrodes 4, 40, 42, 44-48, and 50. IMD 16 may sense such electrical signals via any bipolar combination of electrodes 40, 42, 44-48, and 50. Furthermore, any of the electrodes 40, 42, 44-48, and 50 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac leads 18, 20 and 22, system 10 may include one or more epicardial or extravascular (e.g., subcutaneous or substernal) leads not positioned within heart 12.

In accordance with the techniques of the disclosure, IMD 16 senses parametric data from patient 14. IMD 16 performs a first analysis of the parametric data to determine whether patient 14 is experiencing a treatable event. In some examples, IMD 16 determines whether patient 14 is experiencing cardiac arrhythmia, such as bradycardia, tachycardia, or fibrillation. In some examples, the treatable event is an urgent event that requires immediate delivery of therapy (e.g., within seconds or minutes after detection). In some examples, the treatable event is a non-urgent event that does not require immediate delivery of therapy (e.g., therapy may be delivered within minutes, hours, or days after detection). In some examples, IMD 16 performs feature detection on the parametric data to identify the treatable event. In examples where the treatable event is a cardiac arrhythmia event, IMD 16 may perform feature detection on cardiac electrogram data IMD 16 may compare features of the parametric data to one or more criteria to detect a treatable event.

In some examples, upon determining that patient 14 is experiencing a treatable event, IMD 16 determines that IMD 16 should deliver therapy to patient 14 to provide therapy for the treatable event. For example, upon determining that patient 14 is experiencing a cardiac arrhythmia event, IMD 16 determines that IMD 16 should deliver therapy, e.g., cardiac pacing or shock therapy to patient 14. Prior to delivering the therapy, IMD 16 attempts to establish a wireless connection to external device 27. If IMD 16 is unable to establish the wireless connection to external device 27, IMD 16 proceeds to deliver therapy to patient 14.

If IMD 16 is able to establish the wireless connection to external device 27, then IMD 16 transmits the parametric data to external device 27 for a second analysis of the parametric data by external device 27 to verify the occurrence of the treatable event. IMD 16 may commence delivery of therapy to patient 14. In some examples, IMD 16 receives, from external programmer 27, an instruction configured to cause IMD 16 to proceed with delivery of therapy to patient 14. In response to receiving the instruction, IMD 16 proceeds with delivery of therapy to patient 14. In some examples, IMD 16 receives, from external programmer 27, an instruction configured to cause IMD 16 to abort delivery of therapy to patient 14. In response to receiving the instruction, IMD 16 aborts delivery of therapy to patient 14. In some examples, IMD 16 receives the instruction prior to delivery of therapy and aborts delivery of therapy to patient 14 without delivering therapy to patient 14. In other examples, IMD 16 receives the instruction during delivery of therapy and aborts delivery of therapy to patient 14 during delivering therapy to patient 14.

In some examples, IMD 16 may continue to sense parametric patent data and extend or continue the first analysis of the parametric patient data while external device 27 performs the second analysis. For example, after establishing the wireless connection, IMD 16 may analyze a relatively larger amount of parametric data, and/or perform an analysis that requires a relatively longer amount of time to complete. This may allow IMD 16 to have higher specificity in classifying treatable events because more data is analyzed. Furthermore, IMD 16 may provide additional time to external device 27 such that external device 27 may have sufficient time to receive the parametric data, analyze the transmitted parametric data, verify the determination by IMD 16 to deliver therapy to the patient, and instruct IMD 16 whether to proceed with delivery of therapy.

Although described herein in the context of example IMD 16 that provides electrical therapy, the techniques disclosed herein may be used with other types of devices. For example, the techniques may be implemented with one or more of an extra-cardiac defibrillator coupled to electrodes outside of the heart or outside of the cardiovascular system, a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Figure 3:
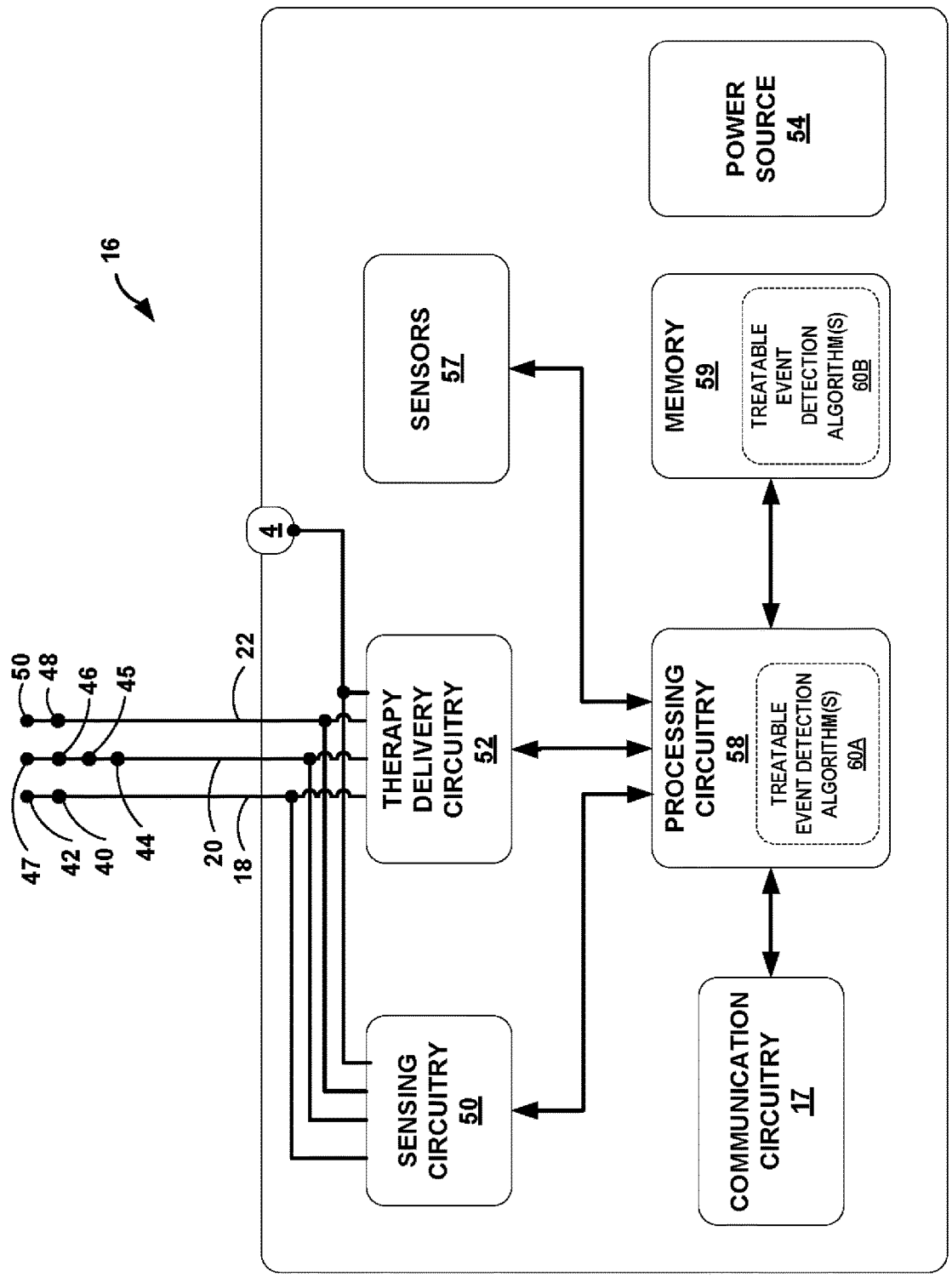
FIG. 3 is a block diagram of an example implantable medical device according to the techniques of the disclosure.

FIG. 3 is a block diagram of example configuration of IMD 16 according to the techniques of the disclosure. In the illustrated example, IMD 16 includes processing circuitry 58, memory 59, communication circuitry 17, sensing circuitry 50, therapy delivery circuitry 52, sensors 57, and power source 54. Memory 59 includes computer-readable instructions that, when executed by processing circuitry 58, cause IMD 16 and processing circuitry 58 to perform various functions attributed to IMD 16 and processing circuitry 58 herein (e.g., performing cardiac arrhythmia detection and delivering therapy, such as anti-tachycardia pacing, bradycardia pacing, and post-shock pacing therapy, etc.). Memory 59 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 58 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 58 may include multiple components, such as any combination of one or more microprocessors, one or more controllers, one or more DSPs, one or more ASICs, or one or more FPGAs, as well as other discrete or integrated logic circuitry. The functions attributed to processing circuitry 58 herein may be embodied as software, firmware, hardware or any combination thereof.

Processing circuitry 58 controls therapy delivery circuitry 52 to deliver therapy to heart 12 according to therapy parameters, which may be stored in memory 59. For example, processing circuitry 58 may control therapy delivery circuitry 52 to deliver electrical pulses with the amplitudes, pulse widths, frequency, or electrode polarities specified by the therapy parameters. In this manner, therapy delivery circuitry 52 may deliver pacing pulses (e.g., ATP pulses, bradycardia pacing pulses, or post-shock pacing therapy) to heart 12 via one or more of electrodes 4, 40, 42, 44-48, and 50. In some examples, therapy delivery circuitry 52 may deliver pacing stimulation, e.g., ATP therapy, bradycardia therapy, or post-shock pacing therapy, in the form of voltage or current electrical pulses. In other examples, therapy delivery circuitry 52 may deliver one or more of these types of stimulation in the form of other signals, such as sine waves, square waves, or other substantially continuous time signals.

In some examples, processing circuitry 58 may implement one or more treatable event detection algorithms 60A stored by memory 59 as treatable event detection algorithms 60B (collectively, treatable event detection algorithms 60). Processing circuitry 58 applies a treatable event detection algorithm 60 to sensed parametric data to determine whether the sensed parametric data is indicative of a treatable event, such as a cardiac arrhythmia. As described in more detail below, each of the treatable event detection algorithms 60 may, e.g., analyze parametric data over different lengths of time, require different amounts of computational resources, have higher or lower specificity, etc.

Therapy delivery circuitry 52 is electrically coupled to electrodes 4, 40, 42, 44-48, and 50. In other examples, IMD 16 may utilize other numbers of electrodes not depicted in FIG. 3. IMD 16 may use any combination of electrodes to deliver therapy and/or detect electrical signals from patient 12. In some examples, therapy delivery circuitry 52 includes a charging circuit, one or more pulse generators, capacitors, transformers, switching modules, and/or other components capable of generating and/or storing energy to deliver as pacing therapy, cardiac resynchronization therapy, other therapy or a combination of therapies. In some examples, therapy delivery circuitry 52 delivers therapy as one or more electrical pulses according to one or more therapy parameter sets defining an amplitude, a frequency, a voltage or current of the therapy, or other parameters of the therapy.

Sensing circuitry 50 monitors signals from one or more combinations (also referred to as vectors) of two or more electrodes from among electrodes 4, 40, 42, 44-48, and 50 in order to monitor electrical activity of heart 12, impedance, or other electrical phenomenon. In some examples, sensing circuitry 50 includes one or more analog components, digital components or a combination thereof. In some examples, sensing circuitry 50 includes one or more sense amplifiers, comparators, filters, rectifiers, threshold detectors, analog-to-digital converters (ADCs) or the like. In some examples, sensing circuitry 50 converts sensed signals to digital form and provides the digital signals to processing circuitry 58 for processing or analysis. In one example, sensing circuitry 50 amplifies signals from electrodes 4, 40, 42, 44-48, and 50 and converts the amplified signals to multi-bit digital signals by an ADC.

In some examples, sensing circuitry 50 performs sensing of the cardiac electrogram to determine heart rates or heart rate variability, or to detect arrhythmias (e.g., tachyarrhythmias or bradycardia) or to sense other parameters or events from the cardiac electrogram. Sensing circuitry 50 may also include a switching circuitry to select which of the available electrodes (and the electrode polarity) are used to sense the heart activity, depending upon which electrode combination, or electrode vector, is used in the current sensing configuration. Processing circuitry 58 may control the switching circuitry to select the electrodes that function as sense electrodes and their polarity. Sensing circuitry 50 may include one or more detection channels, each of which may be coupled to a selected electrode configuration for detection of cardiac signals via that electrode configuration. In some examples, sensing circuitry 50 compares processed signals to a threshold to detect the existence of atrial or ventricular depolarizations and indicate the existence of the atrial depolarization (e.g., P-waves) or ventricular depolarizations (e.g., R-waves) to processing circuitry 58. Sensing circuitry 50 may comprise one or more amplifiers or other circuitry for comparison of the cardiac electrogram amplitude to a threshold, which may be adjustable.

Processing circuitry 58 may include a timing and control module, which may be embodied as hardware, firmware, software, or any combination thereof. The timing and control module may comprise a dedicated hardware circuit, such as an ASIC, separate from other processing circuitry 58 components, such as a microprocessor, or a software module executed by a component of processing circuitry 58, which may be a microprocessor or ASIC. The timing and control module may implement programmable counters. If IMD 16 is configured to generate and deliver bradycardia pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Memory 59 may be configured to store a variety of operational parameters, therapy parameters, sensed and detected data, and any other information related to the therapy and treatment of patient 12. In the example of FIG. 3, memory 58 may store sensed cardiac EGMs, e.g., associated with detected or predicted arrhythmias, and therapy parameters that define the delivery of therapy provided by therapy delivery circuitry 52. In other examples, memory 58 may act as a temporary buffer for storing data until it can be uploaded to external device 27 of FIG. 1.

Communication circuitry 17 includes any suitable circuitry, firmware, software, or any combination thereof for communicating with another device, such as external device 27 of FIG. 1. For example, communication circuitry 17 may include one or more antennae, modulation and demodulation circuitry, filters, amplifiers, or the like for radio frequency communication with other devices, such as external device 27. Under the control of processing circuitry 58, communication circuitry 17 may receive downlink telemetry from and send uplink telemetry to external device 27 with the aid of an antenna, which may be internal and/or external. Processing circuitry 58 may provide the data to be uplinked to external device 27 and the control signals for the telemetry circuit within communication circuitry 17, e.g., via an address/data bus. In some examples, communication circuitry 17 may provide received data to processing circuitry 58 via a multiplexer.

Power source 54 may be any type of device that is configured to hold a charge to operate the circuitry of IMD 16. Power source 54 may be provided as a rechargeable or non-rechargeable battery. In other example, power source 54 may incorporate an energy scavenging system that stores electrical energy from movement of IMD 16 within patient 14.

In accordance with the techniques of the disclosure, processing circuitry 58 senses, via sensing circuitry 50 and/or sensors 57, parametric data from patient 14. Sensors 57 may include one or more sensors, such as one or more accelerometers, pressure sensors, optical sensors for 02 saturation, etc. In some examples, the parametric data includes one or more of an activity level of the patient, a heart rate of the patient, a posture of the patient, a cardiac electrogram of the patient, a blood pressure of the patient, accelerometer data for the patient, or other types of parametric data. The activity level may, in some examples, be a summation of activity over a period of time, such as one or more seconds or minutes.

Processing circuitry 58 analyzes the parametric data to determine whether patient 14 is experiencing a treatable event. In some examples, the treatable event is an urgent event that requires immediate delivery of therapy (e.g., within seconds or minutes after detection). In some examples, the treatable event is a non-urgent event that does not require immediate delivery of therapy (e.g., therapy may be delivered within minutes, hours, or days after detection). In some examples, the treatable event is an occurrence of cardiac arrhythmia, such as bradycardia, tachycardia, or fibrillation. In some examples, processing circuitry 58 performs feature detection on the parametric data to identify the treatable event. In some examples, processing circuitry 58 performs feature detection on one or more of cardiac electrogram data such as electrocardiogram data, electrode impedance measurements, accelerometer data, temperature data for patient 14, or audio data of a heart of patient 14. In some examples, processing circuitry 58 examines criteria related to an RR interval length and/or a frequency of RR intervals, such as a threshold RR length, to detect a cardiac arrhythmia and/or classify the cardiac arrhythmia as a treatable event.

In some examples, upon determining that patient 14 is experiencing a treatable event, processing circuitry 58 determines that IMD 16 should deliver therapy to patient 14 to provide therapy for the treatable event. For example, upon determining that patient 14 is experiencing a cardiac arrhythmia event, processing circuitry 58 determines that IMD 16 should deliver therapy, e.g., cardiac pacing or shock therapy to patient 14. Prior to delivering the therapy, processing circuitry 58 attempts to establish, via communication circuitry 17, a wireless connection to external device 27. If processing circuitry 58 is unable to establish the wireless connection to external device 27, processing circuitry 58 proceeds to control therapy delivery circuitry 52 to deliver therapy to patient 14.

If processing circuitry 58 is able to establish the wireless connection to external device 27, then processing circuitry 58 transmits, via communication circuitry 17, at least some of the parametric data to external device 27. Processing circuitry 58 may commence delivery of therapy to patient 14. In some examples, processing circuitry 58 receives, from external programmer 27 via communication circuitry 17, an instruction configured to cause processing circuitry 58 to abort delivery of therapy to patient 14. In response to receiving the instruction, processing circuitry 58 aborts delivery of therapy to patient 14. In some examples, processing circuitry 58 receives the instruction prior to delivery of therapy and aborts delivery of therapy to patient 14 without delivering therapy to patient 14. In other examples, processing circuitry 58 receives the instruction during delivery of therapy and aborts delivery of therapy to patient 14 during delivering therapy to patient 14.

In some examples, if processing circuitry 58 is unable to establish the wireless connection, then processing circuitry 58 may apply event detection algorithms 60 to a relatively smaller amount of parametric data, and/or perform an analysis that requires a relatively shorter amount of time to complete. For example, processing circuitry 58 may perform tachyarrhythmia classification on, e.g., 30 out of a previously sensed 40 heartbeats having an interval no greater than 320 milliseconds. In this fashion, processing circuitry 58 may classify an event as treatable or not treatable and rapidly determine whether therapy should be delivered.

However, if processing circuitry 58 is able to establish the wireless connection, then processing circuitry 58 may continue to sense parametric data and apply event detection algorithms 60 to the updated parametric data while external device 27 performs the second analysis. For example, after establishing the wireless connection, processing circuitry 58 may apply event detection algorithms 60 to analyze a relatively larger amount of parametric data, and/or perform an analysis that requires a relatively longer amount of time to complete. For example, processing circuitry 58 may perform, e.g., tachyarrhythmia classification on, e.g., 90 of a previously-sensed 120 heartbeats having an interval no greater than 320 milliseconds. This may allow IMD 16 to have higher specificity in classifying treatable events because more data is analyzed. Furthermore, IMD 16 may provide additional time to external device 27 such that external device 27 may have sufficient time to receive the parametric data, analyze the transmitted parametric data, verify the determination by processing circuitry 58 to deliver therapy to the patient, and instruct IMD 16 whether to proceed with delivery of therapy.

Figure 4:
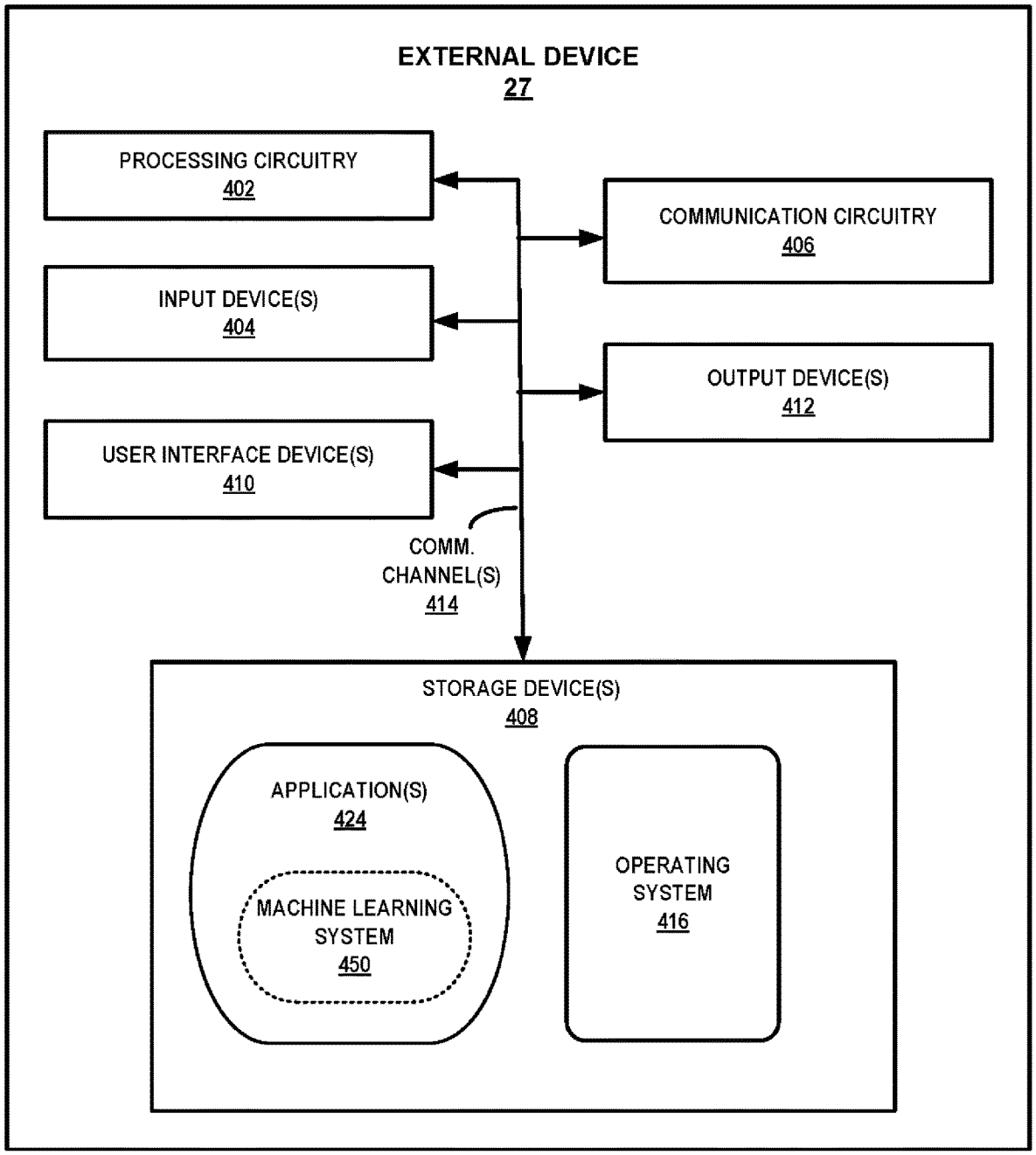
FIG. 4 is a block diagram illustrating an example external device that operates in accordance with one or more techniques of the present disclosure.

FIG. 4 is a block diagram illustrating an example configuration of external device 27 that operates in accordance with one or more techniques of the present disclosure. In some examples, external device 27 takes the form of an external programmer or mobile device, such as a mobile phone, a "smart" phone, a laptop, a tablet computer, a personal digital assistant (PDA), a wearable electronic device, a handheld computing device, computer workstation, server or other networked computing device, etc. In some examples, external device 27 is a CareLink™ monitor available from Medtronic, Inc.

In one example, external device 27 includes processing circuitry 402 for executing applications 424 that include machine learning system 450 or any other applications described herein. Although shown in FIG. 4 as a stand-alone external device 27 for purposes of example, external device 27 may be any component or system that includes processing circuitry or other suitable computing environment for executing software instructions and, for example, need not necessarily include one or more elements shown in FIG. 4 (e.g., communication circuitry 406; and in some examples components such as storage device(s) 408 may not be co-located or in the same chassis as other components).

As shown in the example of FIG. 4, external device 27 includes processing circuitry 402, one or more input devices 404, communication circuitry 406, one or more output devices 412, one or more storage devices 408, and user interface (UI) device(s) 410. External device 27, in one example, further includes one or more application(s) 424 such as machine learning system 450, and operating system 416 that are executable by external device 27. Each of components 402, 404, 406, 408, 410, and 412 are coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within external device 27. For example, processing circuitry 402 may be capable of processing instructions stored in storage device 408. Examples of processing circuitry 402 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within external device 27 during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include random access memories (RAM), dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on external device 27 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

External device 27, in some examples, also includes communication circuitry 406. External device 27, in one example, utilizes communication circuitry 406 to communicate with external devices, such as IMD 16 of FIG. 1. Communication circuitry 406 may include a network interface card, such as an Ethernet card, an optical transceiver, a radio frequency transceiver, or any other type of device that can send and receive information. Other examples of such network interfaces may include 3G, 4G, 5G, and WiFi radios.

External device 27, in one example, also includes one or more user interface devices 410. User interface devices 410, in some examples, are configured to receive input from a user through tactile, audio, or video feedback. Examples of user interface device(s) 410 include a presence-sensitive display, a mouse, a keyboard, a voice responsive system, video camera, microphone or any other type of device for detecting a command from a user. In some examples, a presence-sensitive display includes a touch-sensitive screen.

One or more output devices 412 may also be included in external device 27. Output device 412, in some examples, is configured to provide output to a user using tactile, audio, or video stimuli. Output device 412, in one example, includes a presence-sensitive display, a sound card, a video graphics adapter card, or any other type of device for converting a signal into an appropriate form understandable to humans or machines. Additional examples of output device 412 include a speaker, a cathode ray tube (CRT) monitor, a liquid crystal display (LCD), or any other type of device that can generate intelligible output to a user.

External device 27 may include operating system 416. Operating system 416, in some examples, controls the operation of components of external device 27. For example, operating system 416, in one example, facilitates the communication of one or more applications 424 and machine learning system 450 with processing circuitry 402, communication circuitry 406, storage device 408, input device 404, user interface devices 410, and output device 412.

Application 424 may also include program instructions and/or data that are executable by external device 27. Example application(s) 424 executable by external device 27 may include machine learning system 450. Other additional applications not shown may alternatively or additionally be included to provide other functionality described herein and are not depicted for the sake of simplicity.

In accordance with the techniques of the disclosure, applications 424 include machine learning system 450. In one example, processing circuitry 402 executes machine learning system 450 to determine whether patient 14 of FIG. 1 is experiencing a treatable event, such as a cardiac arrhythmia event. External device 27 may use machine learning system 450 to verify a determination by IMD 16 of FIG. 1 that patient 14 is experiencing the treatable event.

In one example, machine learning system 450 applies a machine learning model to the parametric data for patient 14 to determine, e.g., whether or not the parametric data is indicative of patient 14 experiencing a cardiac arrhythmia event. In some examples, machine learning system 450 further generates a confidence in the determination of whether patient 14 is experiencing a cardiac arrhythmia event.

In some examples, the machine learning model is generated by a neural network system, a deep learning system, or other type of supervised or unsupervised machine learning system. For example, the machine learning model may be generated by a feedforward neural network, such as a convolutional neural network, a radial basis function neural network, a recurrent neural network, a modular or associative neural network. In some examples, machine learning system 450 trains the machine learning model with parametric data for a plurality of patients to generate the determination of whether patient 14 is experiencing a cardiac arrhythmia event. In some examples, after the machine learning model has been pre-trained with the parametric data for the plurality of patients, machine learning system 450 further trains the machine learning model with parametric data specific to patient 14.

In some examples, machine learning system 450 trains the machine learning model with the parametric data for the plurality of patients, determines an error rate of the machine learning model, and then feeds the error rate back to the machine learning model so as to allow the machine learning model to update its predictions based on the error rate. In some examples, machine learning system 450 may receive, e.g., from a clinician, feedback indicating whether a cardiac arrhythmia event detected by machine learning system 450 actually occurred in patient 14. In some examples, machine learning system 450 may receive, from IMD 16, a message indicating that IMD 16 has detected (or has not detected) a cardiac arrhythmia event in patient 14. Machine learning system 450 may update the machine learning model with the feedback indicating whether the detected cardiac arrhythmia actually occurred in patient 14. Thus, the training process may occur iteratively so as to incrementally improve arrhythmia detection made by the machine learning model by "learning" from correct and incorrect analysis of the parametric data made by the machine learning model in the past. Further, the training process may be used to further fine-tune a machine learning model that is trained using population-based data to provide more accurate predictions for a particular individual (e.g., patient 14).

Once the machine learning model has been trained to detect treatable events from parametric data for patient 14 that are of a threshold accuracy selected by the clinician, machine learning system 450 may use the machine learning model to provide detection of cardiac arrhythmias of patient 14. For example, machine learning system 450, executed by processing circuitry 402, receives, via communication circuitry 406, parametric data collected by IMD 16. In some examples, machine learning system 450 may also receive other parametric data collected by external device 27, such as geographic location, accelerometer data, or input from patient 14. In some examples, the parametric data includes one or more of an activity level of the patient, a heart rate of the patient, a posture of the patient, a cardiac electrogram of the patient, a blood pressure of the patient, accelerometer data for the patient, or other types of parametric data. In other examples, external device 27 receives parametric data for patient 14 from other devices, such as a wearable medical device, wearable sensors, or a mobile device (e.g., a smartphone) of patient 14.

Machine learning system 450 applies the trained machine learning model to the parametric data to detect treatable events occurring in patient 14. In some examples, external device 27 uses machine learning system 450 to verify the detection of treatable events by IMD 16 of FIG. 1. For example, the machine learning model converts the parametric data into one or more vectors and tensors (e.g., multi-dimensional arrays) that represent the parametric data. The machine learning model may apply mathematical operations to the one or more vectors and tensors to generate a mathematical representation of the parametric data. The machine learning model may determine different weights that correspond to identified relationships between the parametric data and an occurrence of cardiac arrhythmia. The machine learning model may apply the different weights to the parametric data to generate a determination of whether or not a cardiac arrhythmia event is present in the parametric data and a confidence in the determination.

In the foregoing example, external device 27 implements machine learning system 450 to determine whether patient 14 is experiencing a treatable event. In other examples, external device 27 may instead apply feature detection to the parametric data to determine whether patient 14 is experiencing a treatable event in a similar fashion as IMD 16 applies feature detection to parametric data as described above.

In an example where the treatable event is a cardiac arrhythmia event, processing circuitry 402 performs feature detection on parametric data, including electrocardiogram data. In this example, the parametric data includes one or more of an average frequency or an average amplitude of a T-wave of an electrocardiogram of patient 14. Processing circuitry 402 receives a raw electrocardiogram signal from IMD 16, and extracts features from the raw electrocardiogram signal. In some examples, processing circuitry 402 identifies one or more of T-wave alternans, QRS morphology measures, etc. For example, processing circuitry 402 identifies one or more features of a T-wave of an electrocardiogram of patient 14 and applies a model to the one or more identified features to determine whether patient 14 is experiencing a cardiac arrhythmia event. In some examples, the one or more identified features are one or more amplitudes of the T-wave. In some examples, the one or more identified features are a frequency of the T-wave. In some examples, the one or more identified features include at least an amplitude of the T-wave and a frequency of the T-wave.

While IMD 16 may perform relatively less complex algorithms to detect treatable events due to battery and processing power constraints, external device 27 may not be so limited. For example, external device 27 may be easily charged, a larger battery, or have significantly more computing resources. Therefore, external device 27 may apply an algorithm that is more computationally-expensive, algorithmically complex, consumes more power, or analyzes parametric data over a longer period of time than IMD 16 (e.g., minutes or hours for external device 27 versus seconds or minutes for IMD 16).

In some examples, processing circuitry 402 confirms (e.g., via machine learning system 450 or via feature detection) that IMD 16 has correctly determined that the parametric data indicates a treatable event occurring in patient 14. In one example, processing circuitry 402 transmits an instruction to IMD 16 to cause IMD 16 to proceed with delivery of therapy to patient 14. In another example, processing circuitry 402 may take no action so as to allow IMD 16 to proceed with delivery of therapy to patient 14 according to the internal instructions of IMD 16.

In some examples, processing circuitry 402 determines (e.g., via machine learning system 450 or via feature detection) that IMD 16 has incorrectly determined that the parametric data indicates a treatable event and that no treatable event is occurring within patient 14. In some examples, if processing circuitry 406 determines that IMD 16 has not yet commenced delivery of therapy to patient 14 or is currently delivering therapy to patient 14, processing circuitry 402 transmits, via communication circuitry 406 and to IMD 16, an instruction configured to cause IMD 16 to abort delivery of therapy to patient 14. The instruction may cause IMD 16 to abort delivery of therapy to patient 14 either prior to delivering therapy or mid-delivery of therapy to patient 14. In some examples, processing circuitry 402 determines that the parametric data does not indicate that patient 14 is experiencing the treatable event but IMD 16 is already delivering or has delivered therapy to patient 14, and so may forego causing IMD 16 to abort delivery of therapy. In this fashion, external device 27 may provide increased accuracy and specificity to an analysis of parametric data to verify determinations by IMD 16 of whether or not patient 14 is experiencing treatable events.

Figure 5A:
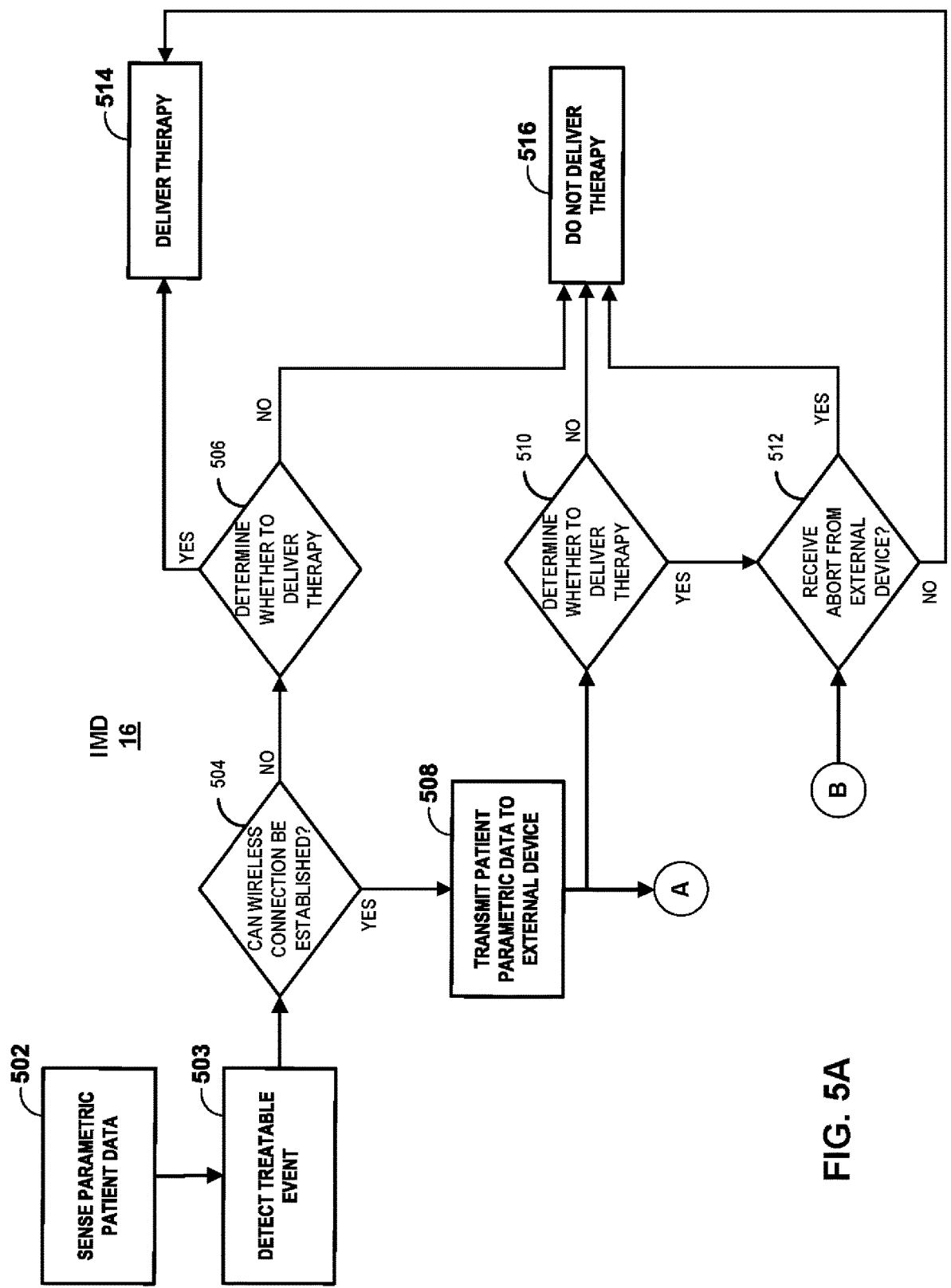
FIGS. 5A and 5B are flowcharts illustrating an example operation in accordance with the techniques of the disclosure.
Figure 5B:
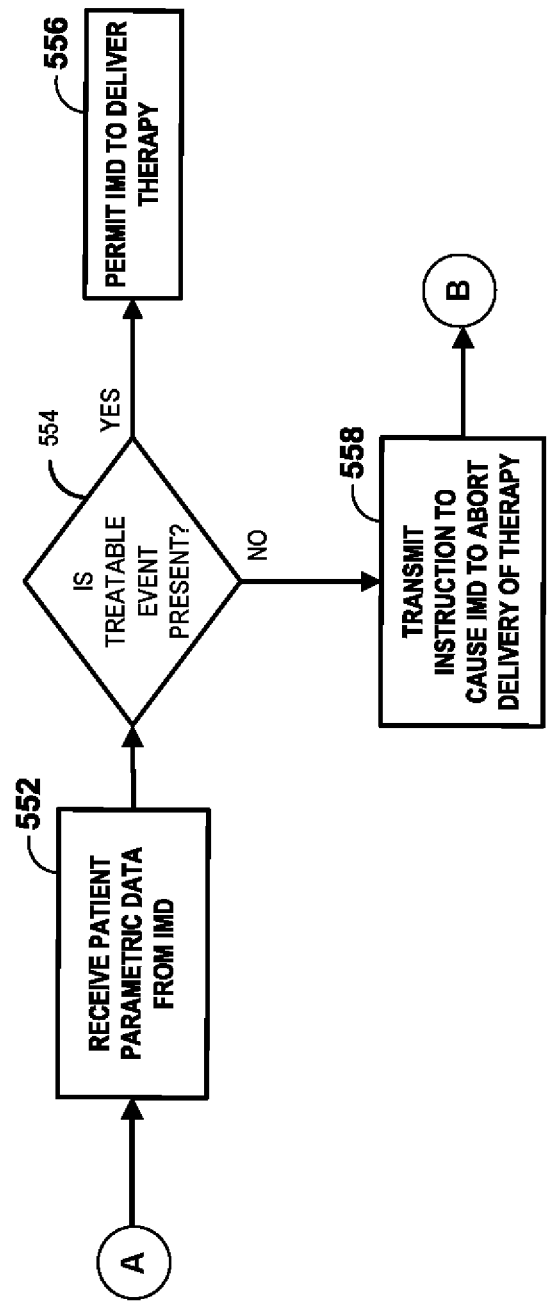

FIGS. 5A and 5B are flowcharts illustrating an example operation in accordance with the techniques of the disclosure. For convenience, FIG. 5A is described with respect to IMB 16 of FIGS. 1-3, and FIG. 5B is descried with respect to external device 27 of FIGS. 1 and 4. In some examples, the operation of FIGS. 5A-5B is an operation for providing multi-tier detection of treatable events, such as cardiac arrhythmia events, in patient 14.

As depicted in the example of FIG. 5A, processing circuitry 58 of IMB 16 senses, via sensing circuitry 50 and/or sensors 57, parametric data from patient 14 (502). In some examples, the parametric data includes one or more of an activity level of the patient, a heart rate of the patient, a posture of the patient, a cardiac electrogram of the patient, a blood pressure of the patient, accelerometer data for the patient, or other types of parametric data. The activity level may, in some examples, be a summation of activity over a period of time, such as one or more seconds or minutes.

Processing circuitry 58 analyzes the parametric data to detect a treatable event (503). In some examples, processing circuitry 58 determines whether the parametric data is indicative of a cardiac arrhythmia event. In response to determining that the patient is experiencing a treatable event, processing circuitry 58 attempts to establish, via communication circuitry 17, a wireless connection to external device 27 (504). If processing circuitry 58 is unable to establish the wireless connection to external device 27 (e.g., "NO" block of 504), processing circuitry 58 determines whether to deliver therapy to patient 14 (506). In some examples, processing circuitry 58 classifies the treatable event to determine if delivery of therapy is appropriate for the type of treatable event. For example, processing circuitry 58 performs feature detection on the parametric data to classify, e.g., a cardiac arrhythmia event as tachycardia or fibrillation. In some examples, processing circuitry 58 performs feature detection on one or more of cardiac electrogram data such as electrocardiogram data, electrode impedance measurements, accelerometer data, temperature data for patient 14, or audio data of a heart of patient 14. In some examples, where processing circuitry 58 is unable to establish the wireless connection to external device 27, processing circuitry 58 may perform a first algorithm of low complexity to classify the cardiac arrhythmia. For example, processing circuitry 58 may perform, e.g., tachyarrhythmia classification using, e.g., 30 out of a previously sensed 40 heartbeats having an interval no greater than 320 milliseconds.

In response to determining that IMD 16 should delivery therapy (e.g., "YES" block of 506), processing circuitry 58 controls therapy delivery circuitry 52 to deliver therapy to patient 14 (514). For example, upon determining that patient 14 is experiencing a cardiac arrhythmia event, processing circuitry 58 controls therapy delivery circuitry 52 to deliver therapy, e.g., cardiac pacing or shock therapy to patient 14. In response to determining that IMD 16 should not delivery therapy (e.g., "NO" block of 506), processing circuitry 58 does not take action and does not deliver therapy to patient 14 at the present time (516).

If processing circuitry 58 is able to establish the wireless connection to external device 27 (e.g., "YES" block of 504), then processing circuitry 58 transmits, via communication circuitry 17, the parametric data to external device 27 via the wireless connection (e.g., element "A" of FIGS. 5A and 5B) (508).

Furthermore, after establishing the wireless connection and transmitting the parametric data, processing circuitry 58 determines whether to deliver therapy to patient 14 (510). For example, processing circuitry 58 classifies the treatable event to determine if delivery of therapy is appropriate for the type of treatable event. In some examples, processing circuitry 58 performs feature detection on the parametric data to classify, e.g., a cardiac arrhythmia event as tachycardia or fibrillation. In some examples, processing circuitry 58 performs feature detection on one or more of cardiac electrogram data such as electrocardiogram data, electrode impedance measurements, accelerometer data, temperature data for patient 14, or audio data of a heart of patient 14. In some examples, processing circuitry 58 transmits, via communication circuitry 17, an indication to external device 27 that processing circuitry 58 has determined, based on the analysis of the parametric data, that the patient is experiencing a treatable event.

In some examples, where processing circuitry 58 is able to establish the wireless connection to external device 27, processing circuitry 58 may continue analysis of the parametric data to classify the treatable event. For example, processing circuitry 58 may perform, e.g., tachyarrhythmia classification using, e.g., 90 of a previously-sensed 120 heartbeats having an interval no greater than 320 milliseconds. This may allow IMD 16 to have higher specificity in classifying treatable events because more data is analyzed. Furthermore, IMD 16 may provide additional time to external device 27 such that external device 27 may have sufficient time to receive the parametric data, analyze the transmitted parametric data, verify the determination by IMD 16 to deliver therapy to the patient, and instruct IMD 16 whether to proceed with delivery of therapy (as described in FIG. 5B below).

In response to determining that IMD 16 should not delivery therapy (e.g., "NO" block of 510), processing circuitry 58 does not take action and does not deliver therapy to patient 14 at the present time (516). In response to determining that IMD 16 should delivery therapy (e.g., "YES" block of 510), processing circuitry 58 determines whether IMD 16 has received an abort instruction from external device 27 (e.g., element "B" of FIGS. 5A and 5B) (512). In response to determining that IMD 16 has received an abort instruction from external device 27 (e.g., "YES" block of 516), processing circuitry 58 does not take action and does not deliver therapy to patient 14 at the present time (516). In some examples, the instruction to abort delivery of therapy received from external device 27 may override the determination by processing circuitry 58 that the cardiac arrhythmia event requires IMD 16 to deliver therapy to patient 14.

In response to determining that IMD 16 has received an abort instruction from external device 27 (e.g., "YES" block of 516), processing circuitry 58 controls therapy delivery circuitry 52 to deliver therapy to patient 14 (514). For example, upon determining that patient 14 is experiencing a cardiac arrhythmia event, processing circuitry 58 controls therapy delivery circuitry 52 to deliver therapy, e.g., cardiac pacing or shock therapy to patient 14. In some examples, processing circuitry 58 receives the instruction to abort delivery of therapy during delivery of therapy. In such an example, processing circuitry 58 may abort delivery of therapy to patient 14 during delivering therapy to patient 14.

As depicted in the example of FIG. 5B, external programmer 27 receives, from IMD 16 via the wireless connection (e.g., element "A" of FIGS. 5A and 5B), the parametric data (552). In some examples, the wireless connection is established according to one of Bluetooth® or BLE®. External programmer 27 determines whether a treatable event is present within the parametric data (554). In some examples, processing circuitry 402 of external device 27 applies machine learning system 450 to the parametric data to determine, e.g., whether or not the parametric data is indicative of patient 14 experiencing a cardiac arrhythmia event. In some examples, machine learning system 450 further generates a confidence in the determination of whether patient 14 is experiencing a cardiac arrhythmia event. In some examples, processing circuitry 402 applies feature detection to the parametric data to determine whether patient 14 is experiencing the treatable event. In this fashion, external device 27 may verify the determination by IMD 16 that a treatable event, such as a cardiac arrhythmia event, is present within the parametric data.

In response to confirming that a treatable event is present within the parametric data (e.g., "YES" block of 554), processing circuitry 402 confirms that IMD 16 has correctly determined that the parametric data indicates a treatable event. Processing circuitry 402 may take no action so as to permit IMD 16 to deliver therapy to patient 14 (556). In other examples, processing circuitry 402 may transmit a message to IMD 16 confirming that IMD 16 has correctly determined that the parametric data indicates a treatable event such that IMD 16 may immediately proceed with delivery of therapy without waiting for a response from external programmer 27 to time out.

In response to determining that a treatable event is not present within the parametric data (e.g., "NO" block of 554), processing circuitry 402 determines that IMB 16 has incorrectly detected a treatable event. In some examples, if processing circuitry 406 determines that IMB 16 has not yet commenced delivery of therapy to patient 14 or is currently delivering therapy to patient 14, processing circuitry 402 transmits, via communication circuitry 406 and to IMD 16 (e.g., element "B" of FIGS. 5A and 5B), an instruction configured to cause IMD 16 to abort delivery of therapy to patient 14 (558). In some examples, processing circuitry 402 determines that the parametric data does not indicate that patient 14 is experiencing the treatable event but IMD 16 is already delivering or has delivered therapy to patient 14, and so takes no action. In this fashion, external device 27 may provide increased accuracy and specificity to an analysis of parametric data to verify determinations by IMD 16 of whether or not patient 14 is experiencing treatable events.

The following examples may illustrate one or more aspects of the disclosure.

EXAMPLE 1

A method comprising: sensing, by a first device, parametric data for a patient; determining, by the first device and based on a first analysis of the parametric data, that the patient is experiencing a treatable event; in response to determining that the patient is experiencing the treatable event, determining, by the first device, whether a second device is available for wireless communication; in response to determining that the second device is available for wireless communication, transmitting, from the first device to the second device, at least a portion of the parametric data for a second analysis of the at least a portion of the parametric data by the second device; and receiving, by the first device and from the second device, an instruction for responding to the treatable event, the instruction selected based on the second analysis of the at least a portion of the parametric data by the second device.

EXAMPLE 2

The method of example 1, wherein the second analysis of the at least a portion of the parametric data by the second device indicates that the patient is not experiencing the treatable event, wherein receiving, by the first device and from the second device, the instruction for responding to the treatable event comprises receiving, by the first device and from the second device, an instruction to abort delivery of a therapy to the patient to treat the treatable event, and wherein the method further comprises determining, by the first device and in response to determining that the patient is experiencing the treatable event, to deliver the therapy to the patient to treat the treatable event; and aborting, by the first device, delivery of the therapy to the patient in response to receiving the instruction to abort delivery of the therapy.

EXAMPLE 3

The method of example 2, wherein aborting delivery of therapy to the patient comprises one of: aborting, by the first device, delivery of therapy to the patient prior to the delivery of therapy to the patient; or aborting, by the first device, delivery of therapy to the patient during the delivery of therapy to the patient.

EXAMPLE 4

The method of example 1, wherein the second analysis of the at least a portion of the parametric data by the second device indicates that the patient is experiencing the treatable event, wherein receiving, by the first device and from the second device, the instruction for responding to the treatable event comprises receiving, by the first device and from the second device, an instruction to deliver a therapy to the patient to treat the treatable event, and wherein the method further comprises: determining, by the first device and in response to determining that the patient is experiencing the treatable event, to deliver the therapy to the patient to treat the treatable event; and delivering, by the first device, the therapy to the patient in response to receiving the instruction to deliver the therapy.

EXAMPLE 5

The method of any of examples 1 through 4, further comprising: sensing, by the first device and during the second analysis of the at least a portion of the parametric data by the second device, additional parametric data for the patient; continuing, by the first device, the first analysis of the parametric data and the additional parametric data until one of: the first device receives, from the second device, the instruction for responding to the treatable event; or the first device determines, based on the continued first analysis of the parametric data, that the patient is experiencing the treatable event.

EXAMPLE 6

The method of any of examples 1 through 5, wherein the parametric data comprises cardiac electrogram data, and wherein the first analysis comprises tachyarrhythmia classification by the first device of the parametric data.

EXAMPLE 7

The method of any of examples 1 through 6, wherein determining, based on the first analysis of the parametric data, that the patient is experiencing the treatable event comprises determining, based on the first analysis of the parametric data, that the patient is experiencing a treatable cardiac arrhythmia event, and wherein receiving the instruction for responding to the treatable event comprises receiving an instruction for responding to the treatable cardiac arrhythmia event.

EXAMPLE 8

The method of any of examples 1 through 7, wherein transmitting the at least a portion of the parametric data comprises transmitting, via one of Bluetooth® or Bluetooth® Low Energy (BLE), the at least a portion of the parametric data.

EXAMPLE 9

A first device comprising: sensing circuitry configured to sense parametric data for a patient; processing circuitry configured to: determine, based on a first analysis of the parametric data, that the patient is experiencing a treatable event; and in response to determining that the patient is experiencing the treatable event, determine whether a second device is available for wireless communication; and communication circuitry configured to: transmit, to the second device, at least a portion of the parametric data for a second analysis of the at least a portion of the parametric data by the second device in response to the determination that the second device is available for wireless communication; and receive, from the second device, an instruction for responding to the treatable event, the instruction selected based on the second analysis of the at least a portion of the parametric data by the second device.

EXAMPLE 10

The first device of example 9, wherein the second analysis of the at least a portion of the parametric data by the second device indicates that the patient is not experiencing the treatable event, wherein to receive, from the second device, the instruction for responding to the treatable event, the communication circuitry is configured to receive, from the second device, an instruction to abort delivery of a therapy to the patient to treat the treatable event, and wherein the processing circuitry is further configured to: determine, in response to determining that the patient is experiencing the treatable event, to deliver the therapy to the patient to treat the treatable event; and abort delivery of the therapy to the patient in response to receiving the instruction to abort delivery of the therapy.

EXAMPLE 11

The first device of example 10, wherein to abort delivery of therapy to the patient, the processing circuitry is configured to: abort delivery of therapy to the patient prior to the delivery of therapy to the patient; or abort delivery of therapy to the patient during the delivery of therapy to the patient.

EXAMPLE 12

The first device of example 9, wherein the second analysis of the at least a portion of the parametric data by the second device indicates that the patient is experiencing the treatable event, wherein to receive from the second device, the instruction for responding to the treatable event, the communication circuitry is configured to receive, from the second device, an instruction to deliver a therapy to the patient to treat the treatable event, and wherein the processing circuitry is further configured to: determine, in response to determining that the patient is experiencing the treatable event, to deliver the therapy to the patient to treat the treatable event; and deliver the therapy to the patient in response to receiving the instruction to deliver the therapy.

EXAMPLE 13

The first device of any of examples 9 through 12, wherein the sensing circuitry is further configured to sense, during the second analysis of the at least a portion of the parametric data by the second device, additional parametric data for the patient, and wherein the processing circuitry is configured to continue the first analysis of the parametric data and the additional parametric data until one of: the first device receives, from the second device, the instruction for responding to the treatable event; or the first device determines, based on the continued first analysis of the parametric data, that the patient is experiencing the treatable event.

EXAMPLE 14

The first device of any of examples 9 through 13, wherein the parametric data comprises cardiac electrogram data, and wherein the first analysis comprises tachyarrhythmia classification by the first device of the parametric data.

EXAMPLE 15

The first device of any of examples 9 through 14, wherein to determine, based on the first analysis of the parametric data, that the patient is experiencing the treatable event, the processing circuitry is configured to determine, based on the first analysis of the parametric data, that the patient is experiencing a treatable cardiac arrhythmia event, and wherein to receive the instruction for responding to the treatable event, the communication circuitry is configured to receive an instruction for responding to the treatable cardiac arrhythmia event.

EXAMPLE 16

The first device of any of examples 9 through 15, wherein the first device comprises an implantable medical device, and wherein the second device comprises at least one of an external programmer or a mobile device.

EXAMPLE 17

A method comprising: establishing, by a second device, wireless communication with a first device; receiving, by the second device and from the first device, parametric data for a patient; receiving, by the second device and from the first device, an indication that the first device has determined, based on a first analysis of the parametric data, that the patient is experiencing a treatable event; performing, by the second device, a second analysis of the parametric data to verify whether the patient is experiencing the treatable event; selecting, by the second device and based on the second analysis of the parametric data, an instruction for responding to the treatable event; and transmitting, by the second device and to the first device, the instruction for responding to the treatable event.

EXAMPLE 18

The method of example 17, wherein the second analysis of the parametric data by the second device indicates that the patient is not experiencing the treatable event, and wherein selecting the instruction for responding to the treatable event comprises selecting an instruction to abort delivery of a therapy to the patient to treat the treatable event; and wherein transmitting the instruction for responding to the treatable event comprises transmitting the instruction to abort delivery of the therapy to the patient to treat the treatable event.

EXAMPLE 19

The method of example 17, wherein the second analysis of the parametric data by the second device indicates that the patient is experiencing the treatable event, and wherein selecting the instruction for responding to the treatable event comprises selecting an instruction to deliver a therapy to the patient to treat the treatable event; and wherein transmitting the instruction for responding to the treatable event comprises transmitting the instruction to deliver the therapy to the patient to treat the treatable event.

EXAMPLE 20

The method of any of examples 17 through 19, wherein the treatable event comprises a treatable cardiac arrhythmia event, and wherein transmitting the instruction for responding to the treatable event comprises transmitting an instruction for responding to the treatable cardiac arrhythmia event.

EXAMPLE 21

The method of any of examples 17 through 20, wherein performing the second analysis of the parametric data to verify whether the patient is experiencing the treatable event comprises applying a machine learning system to the parametric data to verify whether the patient is experiencing the treatable event.

EXAMPLE 22

The method of any of examples 17 through 21, wherein the second analysis of the parametric data by the second device indicates that the patient is experiencing the treatable event, and wherein the method further comprises generating, by the second device, a notification that that the patient is experiencing the treatable event in response to the second analysis of the parametric data indicating that the patient is experiencing the treatable event.

EXAMPLE 23

The method of any of examples 17 through 22, wherein the second analysis of the parametric data by the second device indicates that the patient is experiencing the treatable event, and wherein the method further comprises instructing, by the second device, the first device to generate a notification that that the patient is experiencing the treatable event.

EXAMPLE 24

The method of any of examples 17 through 23, wherein the first device comprises an implantable medical device, and wherein the second device comprises at least one of an external programmer or a mobile device.

EXAMPLE 25

A second device comprising: communication circuitry configured to: establish wireless communication with a first device; receive, from the first device, parametric data for a patient; and receive, from the first device, an indication that the first device has determined, based on a first analysis of the parametric data, that the patient is experiencing a treatable event; and processing circuitry configured to: perform a second analysis of the parametric data to verify whether the patient is experiencing the treatable event; and select, based on the second analysis of the parametric data, an instruction for responding to the treatable event, wherein the communication circuitry is further configured to transmit, to the first device, the instruction for responding to the treatable event.

EXAMPLE 26

The second device of example 25, wherein the second analysis of the parametric data by the second device indicates that the patient is not experiencing the treatable event, and wherein to select the instruction for responding to the treatable event, the processing circuitry is configured to select an instruction to abort delivery of a therapy to the patient to treat the treatable event; and wherein to transmit the instruction for responding to the treatable event, the communication circuitry is configured to transmit the instruction to abort delivery of the therapy to the patient to treat the treatable event.

EXAMPLE 27

The second device of example 25, wherein the second analysis of the parametric data by the second device indicates that the patient is experiencing the treatable event, and wherein to select the instruction for responding to the treatable event, the processing circuitry is configured to select an instruction to deliver a therapy to the patient to treat the treatable event; and wherein to transmit the instruction for responding to the treatable event, the communication circuitry is configured to transmit the instruction to deliver the therapy to the patient to treat the treatable event.

EXAMPLE 28

The second device of any of examples 25 through 27, wherein the treatable event comprises a treatable cardiac arrhythmia event, and wherein to transmit the instruction for responding to the treatable event, the communication circuitry is configured to transmit an instruction for responding to the treatable cardiac arrhythmia event.

EXAMPLE 29

The second device of any of examples 25 through 28, wherein the second analysis of the parametric data by the second device indicates that the patient is experiencing the treatable event, and wherein the processing circuitry is further configured to generate a notification that that the patient is experiencing the treatable event in response to the second analysis of the parametric data indicating that the patient is experiencing the treatable event, and wherein the communication circuitry is further configured to transmit the notification that that the patient is experiencing the treatable event.

EXAMPLE 30

A system comprising: a first device configured to: sense parametric data for a patient; determine, based on a first analysis of the parametric data, that the patient is experiencing a treatable event; in response to determining that the patient is experiencing the treatable event, determine whether a second device is available for wireless communication; in response to determining that the second device is available for wireless communication, transmit, to the second device, at least a portion of the parametric data; and the second device configured to: receive the at least a portion of the parametric data; perform a second analysis of the at least a portion of the parametric data to verify whether the patient is experiencing the treatable event; and select, based on the second analysis of the parametric data, an instruction for responding to the treatable event; and transmit, to the first device, the instruction for responding to the treatable event, wherein the first device is further configured to: receive the instruction for responding to the treatable event.

EXAMPLE 31

A computing device comprising: communication circuitry configured to: establish wireless communication with an implantable cardiac monitoring device; receive, from the implantable cardiac monitoring device, parametric data for a patient; and receive, from the implantable cardiac monitoring device, an indication that the implantable cardiac monitoring device has determined, based on a first analysis of the parametric data, that the patient is experiencing a treatable event; and processing circuitry configured to: perform a second analysis of the parametric data to verify whether the patient is experiencing the treatable event, wherein performing the second analysis of the parametric data to verify whether the patient is experiencing the treatable event comprises applying a machine learning system to the parametric data to verify whether the patient is experiencing the treatable event; and generating a notification that that the patient is experiencing the treatable event in response to the second analysis of the parametric data indicating that the patient is experiencing the treatable event.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
    sensing, by a first device, parametric data for a patient;
    determining, by the first device and based on a first analysis of the parametric data, that the patient is experiencing a treatable event;
    in response to determining that the patient is experiencing the treatable event, determining, by the first device, whether a second device is available for wireless communication;
    in response to determining that the second device is available for wireless communication;
        transmitting, from the first device to the second device, at least a portion of the parametric data for a second analysis of the at least a portion of the parametric data by the second device; and
        receiving, by the first device and from the second device, an instruction for responding to the treatable event, the instruction selected based on the second analysis of the at least a portion of the parametric data by the second device; and
    in response to determining that the second device is not available for wireless communication:
        determining, by the first device, whether to deliver therapy to the patient; and
        in response to determining, by the first device, to deliver the therapy to the patient, performing, by the first device, delivery of the therapy.

2. The method of claim 1,
    wherein the second analysis of the at least a portion of the parametric data by the second device indicates that the patient is not experiencing the treatable event,
    wherein receiving, by the first device and from the second device, the instruction for responding to the treatable event comprises receiving, by the first device and from the second device, an instruction to abort delivery of a therapy to the patient to treat the treatable event, and
    wherein the method further comprises
        determining, by the first device and in response to determining that the patient is experiencing the treatable event, to deliver the therapy to the patient to treat the treatable event; and
        aborting, by the first device, delivery of the therapy to the patient in response to receiving the instruction to abort delivery of the therapy.

3. The method of claim 2, wherein aborting delivery of therapy to the patient comprises one of:
    aborting, by the first device, delivery of therapy to the patient prior to the delivery of therapy to the patient; or
    aborting, by the first device, delivery of therapy to the patient during the delivery of therapy to the patient.

4. The method of claim 1,
    wherein the second analysis of the at least a portion of the parametric data by the second device indicates that the patient is experiencing the treatable event,
    wherein receiving, by the first device and from the second device, the instruction for responding to the treatable event comprises receiving, by the first device and from the second device, an instruction to deliver a therapy to the patient to treat the treatable event, and
    wherein the method further comprises:
        determining, by the first device and in response to determining that the patient is experiencing the treatable event, to deliver the therapy to the patient to treat the treatable event; and
    delivering, by the first device, the therapy to the patient in response to receiving the instruction to deliver the therapy.

5. The method of claim 1, further comprising:
    sensing, by the first device and during the second analysis of the at least a portion of the parametric data by the second device, additional parametric data for the patient;
    continuing, by the first device, the first analysis of the parametric data and the additional parametric data until one of:
        the first device receives, from the second device, the instruction for responding to the treatable event; or
        the first device determines, based on the continued first analysis of the parametric data, that the patient is experiencing the treatable event.

6. The method of claim 1,
    wherein the parametric data comprises cardiac electrogram data, and
    wherein the first analysis comprises tachyarrhythmia classification by the first device of the parametric data.

7. The method of claim 1,
    wherein determining, based on the first analysis of the parametric data, that the patient is experiencing the treatable event comprises determining, based on the first analysis of the parametric data, that the patient is experiencing a treatable cardiac arrhythmia event, and wherein receiving the instruction for responding to the treatable event comprises receiving an instruction for responding to the treatable cardiac arrhythmia event.

8. The method of claim 1, wherein transmitting the at least a portion of the parametric data comprises transmitting, via one of Bluetooth® or Bluetooth® Low Energy (BLE), the at least a portion of the parametric data.

9. A first device comprising:
sensing circuitry configured to sense parametric data for a patient;
processing circuitry configured to:
  determine, based on a first analysis of the parametric data, that the patient is experiencing a treatable event; and
  in response to determining that the patient is experiencing the treatable event, determine whether a second device is available for wireless communication;
therapy delivery circuitry; and
communication circuitry,
wherein, in response to the processing circuitry determining that the second device is available for wireless communication, the communication circuitry is configured to:
  transmit, to the second device, at least a portion of the parametric data for a second analysis of the at least a portion of the parametric data by the second device; and
  receive, from the second device, an instruction for responding to the treatable event, the instruction selected based on the second analysis of the at least a portion of the parametric data by the second device; and
wherein, in response to the processing circuitry determining that the second device is not available for wireless communication:
  the processing circuitry is further configured to determine whether to deliver therapy to the patient; and
  in response to the processing circuitry determining to deliver the therapy to the patient, the therapy delivery circuitry is configured to perform delivery of therapy.

10. The first device of claim 9,
wherein the second analysis of the at least a portion of the parametric data by the second device indicates that the patient is not experiencing the treatable event,
wherein to receive, from the second device, the instruction for responding to the treatable event, the communication circuitry is configured to receive, from the second device, an instruction to abort delivery of a therapy to the patient to treat the treatable event, and
wherein the processing circuitry is further configured to:
  determine, in response to determining that the patient is experiencing the treatable event, to deliver the therapy to the patient to treat the treatable event; and
  abort delivery of the therapy to the patient in response to receiving the instruction to abort delivery of the therapy.

11. The first device of claim 10, wherein to abort delivery of therapy to the patient, the processing circuitry is configured to:
abort delivery of therapy to the patient prior to the delivery of therapy to the patient; or
abort delivery of therapy to the patient during the delivery of therapy to the patient.

12. The first device of claim 9,
wherein the second analysis of the at least a portion of the parametric data by the second device indicates that the patient is experiencing the treatable event,
wherein to receive from the second device, the instruction for responding to the treatable event, the communication circuitry is configured to receive, from the second device, an instruction to deliver a therapy to the patient to treat the treatable event, and
wherein the processing circuitry is further configured to:
  determine, in response to determining that the patient is experiencing the treatable event, to deliver the therapy to the patient to treat the treatable event; and
  deliver the therapy to the patient in response to receiving the instruction to deliver the therapy.

13. The first device of claim 9,
wherein the sensing circuitry is further configured to sense, during the second analysis of the at least a portion of the parametric data by the second device, additional parametric data for the patient, and
wherein the processing circuitry is configured to continue the first analysis of the parametric data and the additional parametric data until one of:
  the first device receives, from the second device, the instruction for responding to the treatable event; or
  the first device determines, based on the continued first analysis of the parametric data, that the patient is experiencing the treatable event.

14. The first device of claim 9,
wherein the parametric data comprises cardiac electrogram data, and
wherein the first analysis comprises tachyarrhythmia classification by the first device of the parametric data.

15. The first device of claim 9,
wherein to determine, based on the first analysis of the parametric data, that the patient is experiencing the treatable event, the processing circuitry is configured to determine, based on the first analysis of the parametric data, that the patient is experiencing a treatable cardiac arrhythmia event, and
wherein to receive the instruction for responding to the treatable event, the communication circuitry is configured to receive an instruction for responding to the treatable cardiac arrhythmia event.

16. The first device of claim 9,
wherein the first device comprises an implantable medical device, and
wherein the second device comprises at least one of an external programmer or a mobile device.

17. A method comprising:
establishing, by a second device, wireless communication with a first device;
receiving, by the second device and from the first device, parametric data for a patient sensed by the first device;
receiving, by the second device and from the first device, an indication that the first device has determined, based on a first analysis of a first portion of the parametric data, that the patient is experiencing a treatable event;
performing, by the second device, a second analysis of a second portion of the parametric data sensed by the first device to verify whether the patient is experiencing the treatable event, wherein the second portion of the parametric data sensed by the first device upon which the second analysis is performed is relatively larger than the first portion of the parametric data sensed by the first device upon which the first analysis is performed;

selecting, by the second device and based on the second analysis of the second portion of the parametric data sensed by the first device, an instruction for responding to the treatable event; and transmitting, by the second device and to the first device, the instruction for responding to the treatable event.

18. The method of claim 17, wherein the second analysis of the parametric data by the second device indicates that the patient is not experiencing the treatable event, and wherein selecting the instruction for responding to the treatable event comprises selecting an instruction to abort delivery of a therapy to the patient to treat the treatable event; and wherein transmitting the instruction for responding to the treatable event comprises transmitting the instruction to abort delivery of the therapy to the patient to treat the treatable event.

19. The method of claim 17, wherein the second analysis of the parametric data by the second device indicates that the patient is experiencing the treatable event, and wherein selecting the instruction for responding to the treatable event comprises selecting an instruction to deliver a therapy to the patient to treat the treatable event; and wherein transmitting the instruction for responding to the treatable event comprises transmitting the instruction to deliver the therapy to the patient to treat the treatable event.

20. The method of claim 17, wherein the treatable event comprises a treatable cardiac arrhythmia event, and wherein transmitting the instruction for responding to the treatable event comprises transmitting an instruction for responding to the treatable cardiac arrhythmia event.

21. The method of claim 17, wherein performing the second analysis of the parametric data to verify whether the patient is experiencing the treatable event comprises applying a machine learning system to the parametric data to verify whether the patient is experiencing the treatable event.

22. The method of claim 17, wherein the second analysis of the parametric data by the second device indicates that the patient is experiencing the treatable event, and wherein the method further comprises generating, by the second device, a notification that that the patient is experiencing the treatable event in response to the second analysis of the parametric data indicating that the patient is experiencing the treatable event.

23. The method of claim 17, wherein the second analysis of the parametric data by the second device indicates that the patient is experiencing the treatable event, and wherein the method further comprises instructing, by the second device, the first device to generate a notification that that the patient is experiencing the treatable event.

24. A second device comprising:

communication circuitry configured to:
  establish wireless communication with a first device;
  receive, from the first device, parametric data for a patient sensed by the first device; and
  receive, from the first device, an indication that the first device has determined, based on a first analysis of a first portion of the parametric data, that the patient is experiencing a treatable event; and processing circuitry configured to:
  perform a second analysis of a second portion of the parametric data sensed by the first device to verify whether the patient is experiencing the treatable event, wherein the second portion of the parametric data sensed by the first device upon which the second analysis is performed is relatively larger than the first portion of the parametric data sensed by the first device upon which the first analysis is performed; and
  select, based on the second analysis of the second portion of the parametric data sensed by the first device, an instruction for responding to the treatable event, wherein the communication circuitry is further configured to transmit, to the first device, the instruction for responding to the treatable event.

25. The second device of claim 24, wherein the second analysis of the parametric data by the second device indicates that the patient is not experiencing the treatable event, and wherein to select the instruction for responding to the treatable event, the processing circuitry is configured to select an instruction to abort delivery of a therapy to the patient to treat the treatable event; and wherein to transmit the instruction for responding to the treatable event, the communication circuitry is configured to transmit the instruction to abort delivery of the therapy to the patient to treat the treatable event.

26. The second device of claim 24, wherein the second analysis of the parametric data by the second device indicates that the patient is experiencing the treatable event, and wherein to select the instruction for responding to the treatable event, the processing circuitry is configured to select an instruction to deliver a therapy to the patient to treat the treatable event; and wherein to transmit the instruction for responding to the treatable event, the communication circuitry is configured to transmit the instruction to deliver the therapy to the patient to treat the treatable event.

27. The second device of claim 24, wherein the treatable event comprises a treatable cardiac arrhythmia event, and wherein to transmit the instruction for responding to the treatable event, the communication circuitry is configured to transmit an instruction for responding to the treatable cardiac arrhythmia event.

28. The second device of claim 24, wherein the second analysis of the parametric data by the second device indicates that the patient is experiencing the treatable event, and wherein the processing circuitry is further configured to generate a notification that that the patient is experiencing the treatable event in response to the second analysis of the parametric data indicating that the patient is experiencing the treatable event, and wherein the communication circuitry is further configured to transmit the notification that that the patient is experiencing the treatable event.

29. A system comprising:
a first device comprising:
  first sensing circuitry configured to sense parametric data for a patient;
  first processing circuitry configured to:
    determine, based on a first analysis of the parametric data, that the patient is experiencing a treatable event;
    in response to determining that the patient is experiencing the treatable event, determine whether a second device is available for wireless communication;
  first therapy deliver circuitry; and
  first communication circuitry; and
the second device, wherein the second device comprises:
  second communication circuitry; and
  second processing circuitry,
wherein, in response to the first processing circuitry determining that the second device is available for wireless communication:
  the first communication circuitry is configured to transmit, to the second device, at least a portion of the parametric data for a second analysis of the at least a portion of the parametric data by the second device in response to determining that the second device is available for wireless communication;
  the second communication circuitry is configured to:
    establish wireless communication with the first device; and
    receive the at least a portion of the parametric data;
  the second processing circuitry is configured to:
    perform a second analysis of the at least a portion of the parametric data to verify whether the patient is experiencing the treatable event; and
    select, based on the second analysis of the parametric data, an instruction for responding to the treatable event;
  the second communication circuitry is further configured to transmit, to the first device, the instruction for responding to the treatable event; and
  the first communication circuitry is configured to receive the instruction for responding to the treatable event, and
wherein, in response to the first processing circuitry determining that the second device is not available for wireless communication:
  the first processing circuitry is further configured to determine whether to deliver therapy to the patient; and
  in response to the first processing circuitry determining to deliver the therapy to the patient, the first therapy delivery circuitry is configured to perform delivery of therapy.

30. A computing device comprising:
communication circuitry configured to:
  establish wireless communication with an implantable cardiac monitoring device;
  receive, from the implantable cardiac monitoring device, parametric data for a patient; and
  receive, from the implantable cardiac monitoring device, an indication that the implantable cardiac monitoring device has determined, based on a first analysis of the parametric data, that the patient is experiencing a treatable event; and
processing circuitry configured to:
  perform a second analysis of the parametric data to verify whether the patient is experiencing the treatable event, wherein performing the second analysis of the parametric data to verify whether the patient is experiencing the treatable event comprises applying a machine learning system to the parametric data to verify whether the patient is experiencing the treatable event; and
  causing the implantable cardiac monitoring device to generate a notification that the patient is experiencing the treatable event in response to the second analysis of the parametric data indicating that the patient is experiencing the treatable event.

31. The method of claim 1, further comprising:
establishing, by the second device, wireless communication with the first device;
receiving, by the second device and from the first device, the at least a portion of the parametric data for the patient;
receiving, by the second device and from the first device, an indication that the first device has determined, based on the first analysis of the parametric data, that the patient is experiencing the treatable event;
performing, by the second device, the second analysis of the parametric data to verify whether the patient is experiencing the treatable event;
selecting, by the second device and based on the second analysis of the parametric data, the instruction for responding to the treatable event; and
transmitting, by the second device and to the first device, the instruction for responding to the treatable event.

32. The first device of claim 9, wherein a system further comprises the first device and the second device, wherein the second device comprises:
  second communication circuitry configured to receive the at least a portion of the parametric data; and
  second processing circuitry configured to:
    perform the second analysis of the at least a portion of the parametric data to verify whether the patient is experiencing the treatable event; and
    select, based on the second analysis of the parametric data, the instruction for responding to the treatable event,
  wherein the second communication circuitry is further configured to transmit, to the first device, the instruction for responding to the treatable event.

33. The method of claim 1, wherein determining whether to deliver the therapy to the patient comprises:
  determining, by the first device and based on a third analysis of the parametric data, that the patient is experiencing the treatable event, the third analysis being different from the first analysis; and
  in response to determining, based on the third analysis of the parametric data, that the patient is experiencing the treatable event, performing, by the first device, delivery of the therapy.

34. The method of claim 33,
wherein determining, based on the first analysis of the parametric data, that the patient is experiencing the treatable event comprises determining, based on a first analysis of a first portion of the parametric data, that the patient is experiencing the treatable event, and
wherein determining, based on the third analysis of the parametric data, that the patient is experiencing the treatable event comprises determining, based on a third analysis of a second portion of the parametric data, that the patient is experiencing the treatable event, wherein the second portion of the parametric data is greater than the first portion of the parametric data.

\* \* \* \* \*